US006074644A

United States Patent [19]
Pastan et al.

[11] Patent Number: 6,074,644
[45] Date of Patent: Jun. 13, 2000

[54] NUCLEIC ACIDS ENCODING IMMUNOTOXINS CONTAINING A DISULFIDE-STABILIZED ANTIBODY FRAGMENT REPLACING HALF OR MORE OF DOMAIN IB OF PSEUDOMONAS EXOTOXIN, AND METHODS OF USE OF THE ENCODED IMMUNOTOXINS

[75] Inventors: Ira Pastan, Potomac, Md.; Chien-Tsun Kuan, Chapel Hill, N.C.

[73] Assignee: The United States of America as represented by the Department of Health and Human Services, Washington, D.C.

[21] Appl. No.: 09/397,951

[22] Filed: Sep. 17, 1999

Related U.S. Application Data

[62] Division of application No. 08/809,668, Aug. 21, 1997, which is a continuation of application No. PCT/US96/16327, Oct. 11, 1996.
[60] Provisional application No. 60/005,388, Oct. 13, 1995.

[51] Int. Cl.[7] .......................... A61K 39/395; C07K 16/00
[52] U.S. Cl. .................................... 424/178.1; 424/236.1; 530/387.3; 530/387.7; 536/23.1
[58] Field of Search ............................. 424/178.1, 236.1; 530/387.3, 387.7; 536/23.1

[56] References Cited

U.S. PATENT DOCUMENTS

| | | | |
|---|---|---|---|
| 4,892,827 | 1/1990 | Pastan et al. | 435/193 |
| 4,946,778 | 8/1990 | Ladner et al. | 435/69.6 |
| 5,082,927 | 1/1992 | Pastan et al. | 530/351 |
| 5,091,513 | 2/1992 | Huston et al. | 530/387.3 |
| 5,132,405 | 7/1992 | Huston et al. | 530/387.3 |
| 5,458,878 | 10/1995 | Pastan et al. | 424/260.1 |

FOREIGN PATENT DOCUMENTS

| | | |
|---|---|---|
| 0 338 745 | 10/1989 | European Pat. Off. . |
| 20 91/18099 | 11/1991 | WIPO . |
| WO 93/06217 | 4/1993 | WIPO . |
| WO A 93/07286 | 4/1993 | WIPO . |
| WO 94/29350 | 12/1994 | WIPO . |

OTHER PUBLICATIONS

Batra, et al. Proc. Natl. Acad. Sci. USA, 89:5867–5871 (1992).
Benbar, et al. Prot. Eng. 7(12):1509–1515 (1994).
Bird, et al. Science, 242:423–426 (1988).
Brinkmann, et al. PNAS, USA, 90:7538–7542 (1993).
Brinkmann, et al. J. Immunol. 150:2774–2782 (1993).
Brinkmann et al. Proc. Natl. Acad. Sci. 90:7538–7542 (1993).
Brinkmann, et al. Proc. Natl. Acad. Sci. 88:8616–8620 (1991).
Buchner, et al. Anal. Biochem. 205:264–270 (1992).
Chaudhary, et al. PNAS, USA, 87:308–312 (1990).
Chaudhary, et al. Proc. Natl. Acad. Sci. USA, 84:4538–4542 (1987).
Chaudhary, et al. Proc. Natl. Acad. Sci. USA, 85:2939–2943 (1988).
Chaudhary, et al. Proc. Natl. Acad. Sci. USA, 87:308–312 (1990).
Debinski, Waldemar, et al. (1994) "An Immunotoxin with Increased Activity and Homogeneity Produced by Reducing the Number of Lysine Residues in Recombinant Pseudomonas Exotoxin", Bioconjugate Chemistry, 5(1):40–46.
Dillman, et al. Ann. Internal Medicine. 111:592–600 (1989).
Glockshuber, et al. Biochemistry, 29(6):1362–1367 (1990).
Glockshuber, et al. Biochemistry, 31(5):1270–1279 (1992).
Gray, et al. Proc. Natl. Acad. Sci. USA, 81:2655–2649 (1984).
Harris, et al. TIBTECH 11:42–44 (1993).
Heimbroook, et al. Proc. Natl. Acad. Sci. USA, 87:4697–4701 (1990).
Hird, et al. Chapter 17 in Genes and Cancer, (1990).
Huston, et al. Proc. Natl. Acad. Sci. USA, 85:5879–5883 (1988).
Jinno, et al. J. Biol. Chem. 264:15953–15959 (1989).
Kasprazyk, et al. Cancer Res. 53:2771–2776 (1992).
Kreitman, et al., "Pseudomonas Exotoxin–based Immunotoxins Containing the Antibody LL2 or LL2–Fab' Induce Regression of Subcutaneous Human B–cell Lymphoma in Mice," 819–825 Cancer Research (Feb. 15, 1993).
Kreitman, et al. Bioconjugate Chemistry, pp. 58–62 (1992).
Kreitman, et al. Bioconjugate Chemistry, pp. 63–68 (1992).
Robert J. Kreitman, et al., "The activity of Disulfide–Stabilized Recombinant Immunotoxin RFB4(dsFv)–PE38 towards human CD22+ Lymphoma/Leukemia Xenografts in Mice and Fresh Cells from patients." See Abstract #187, p. 28 Proceedings of the American Association for Cancer Research, (Mar. 1997).
John de Kruif, et al. "Biosynthetically lipid–modified human scFv fragments from phage display libraries as targeting molecules for immunoliposomes," 232–236 Febs. Letters (Dec. 16, 1996).
Kuan, Chien–Tsun, et al. (1996) "Improved anti–tumor activity of a recombinant anti–Lewisy . . ." Proc. Natl. Acad. Sci. USA 93(3), 974–8.

(List continued on next page.)

Primary Examiner—Paula K. Hutzell
Assistant Examiner—Minh-Tam Davis
Attorney, Agent, or Firm—Townsend and Townsend and Crew LLP

[57] ABSTRACT

This invention provides for nucleic acids encoding immunotoxins comprising a Pseudomonas exotoxin (PE) that does not require proteolytic activation for cytotoxic activity attached to an Fv antibody fragment having a variable heavy chain region bound through at least one disulfide bond to a variable light chain region. The combination of a "disulfide-stabilized" binding agent fused to a PE that does not require proteolytic activation provides an immunotoxin having surprising cytotoxic activity.

25 Claims, 5 Drawing Sheets

OTHER PUBLICATIONS

Kuan, Chien–Tsun, et al. (1996) "Recombinant Immunotoxin Containing a Disulfide–Stabilized Fv Directed at erbB2 That does not Require Proteolytic Activation," *Biochemistry*, 35:2872–2877.

Kurucz, et al. *Proc. Natl. Acad. Sci.* 90:3830–3834 (1993).

Lorberboum–Galski, et al. *J. Biol. Chem.* 265:16311–16317 (1990).

Dong Luo, et al., "V1–Linker–Vh Orientation–Dependent Expression of Single Chain Fv Containing an Engineered Disulfide–Stabilized Bond in the Framework Regions," 825–831 *Journal of Biochemistry* (Oct. 1, 1995).

Lyons et al. *Protein Engineering*, 3:703–708 (1990).

Elizabeth Mansfield, et al. "Characterization of RFB4–Pseudomonas Extotoxin A Immunotoxins Targeted to CD22 on B–cell Malignancies," 557–563 *Bioconjugate Chemistry*, (Sep. 5, 1996).

Elizabeth Mansfield, et al., "Recombinant RFB4 Immunotoxins Exhibit Potent Cytotoxic Activity for CD22–Bearing Cells and Tumors," 2020–2026 *Blood* (Sep. 1, 1997).

Ogata, et al. *J. Biol. Chem.* 265:20678–20685 (1990).

Osband, et al. *Immunotherapy* 11(6):193–195 (1990).

Pack et al. *Biochemistry* 31:1579–1584 (1992).

Pantoliano, et al. *Biochemistry*, 30:10117–10125 (1991).

Pastan, et al. *Science*, 254:1173–1177 (1991).

Pluckthun. *Immunological Reviews*, 130:151–188 (1992).

V. Rajagopal, et al. "A form of Anti–Tac(Fv) which is both single–chain and Disulfide–Stabilized for imaging CD25+ Tumors." See Abstract #180, p. 27 *Proceedings of the American Associates for Cancer Research*, (Mar. 1997).

Reiter, et al. *Biochemistry* 33:5451–5459 (1994).

Reiter, et al. *J. Biol. Chem.* 269(28):18327=18331 (1994).

Maria L. Rodriquez, "Development of a Humanized Disulfide–stabilized Anti–p185$^{HER2}$ Fv– β–Lactamase Fusion Protein for Activation of a Cephalosporin Doxorubicin Prodrug," 63–70 *Cancer Research*, (Jan. 1, 1995).

Seetharam, et al. *J. Biol. Chem.* 266:17376–17381 (1991).

Siegall, et al. *J. Biol. Bhem.* 264:14256–14261 (1989).

Siegall, et al. *Biochemistry* 30:7154–7159 (1991).

Stemmer, et al. *Biotechniques*, 14(2):256–265 (1993).

Theuer, Charles P., et al. (1993) "A Recombinant Form of Pseudomonas Exotoxin A Containing Transforming Growth Factor Alpha Near Its Carboxyl Terminus for the Treatment of Bladder Cancer," *The Journal of Urology*, 149:1626–1632.

Theuer, Charles P., et al. (1993) "Immunotoxins Made with a Recombinant Form of Pseudomonas Exotoxin A that do not require proteolysis for activity," *Cancer Research*, 53:340–347.

Theuer, et al. *J. Biol. Chem.* 267:16872–16877 (1992).

Waldman, et al. *Science*, 252:1657–16877 (1991).

Watson, et al. in *Molecular Biology of the Gene*, 4$^{th}$ Ed., Benjamin/Cummings Pub. Co., Menlo Park, CA, p. 313 (1987).

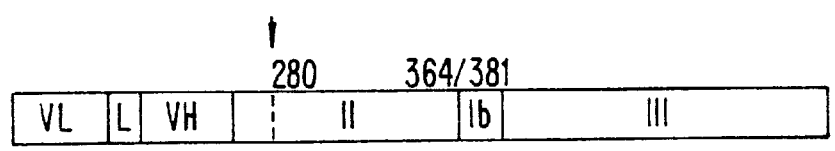
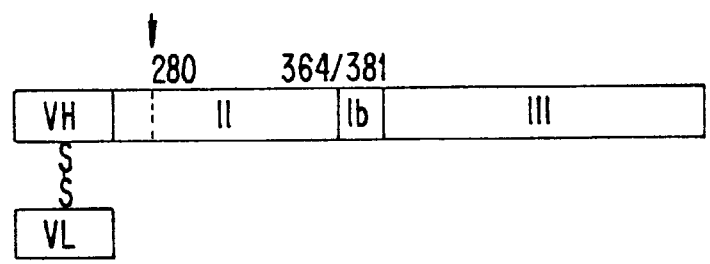
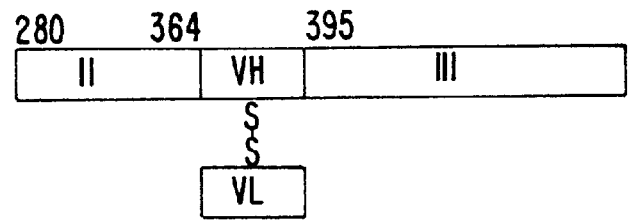
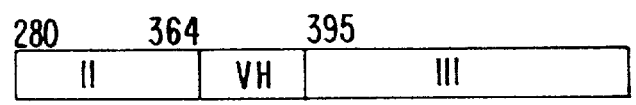
FIG. 1.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 66 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..66
       (D) OTHER INFORMATION: /note= "forward PCR primer CT119"

(xi) SEQUENCE DESCRIPTION: SEQ ID NO:1:

```
GGCAACGACG AGGCCGGCGC GGCCAACGGC GGTGGCGGAT CCGAGGTGCA GCTGGTGGAA      60

TCTGGA                                                                66
```

(2) INFORMATION FOR SEQ ID NO:2:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..51
        (D) OTHER INFORMATION: /note= "reverse PCR primer CT120"

(xi) SEQUENCE DESCRIPTION: SEQ ID NO:2:

GTCGCCGAGG AACTCCGCGC CAGTGGGCTC GGGACCTCCG GAAGCTTTTG C        51

(2) INFORMATION FOR SEQ ID NO:3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AAACCGAGGC CTTCCGGAGG TGGTGGATCC GAAGTGCAGC TGCAGGAGTC AGGA        54

(2) INFORMATION FOR SEQ ID NO:4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTAGCAGCCG AATTCTTAGA GCTCGTCTTT CGGCGGTTTG CCGGAGGAGA CGGTGACCGT        60

GGTCCCTG        68

(2) INFORMATION FOR SEQ ID NO:5:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AAACCGAGGC CTTCCGGAGG TGGTGGATCC GAAGTGCAGC TGCAGGAGTC AGGA        54

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GATCGCTCGG AATTCTTAGG AGACGGTGAC CGTGGTCCCT GC                          42

(2) INFORMATION FOR SEQ ID NO:7:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

TTAGCAGCCG AATTCTTAGA GCTCGTCTTT CGGCGGTTTG CCGGAGGAGA CGGTGACCGT       60

GGTCCCTG                                                                68

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Arg Glu Asp Leu Lys
1               5

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Lys Asp Glu Leu
1

(2) INFORMATION FOR SEQ ID NO:10:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Ser Gly Gly Gly Gly Ser
1               5

(2) INFORMATION FOR SEQ ID NO:11:

(i) SEQUENCE CHARACTERISTICS:
            (A) LENGTH: 7 amino acids
            (B) TYPE: amino acid

```
            (C) STRANDEDNESS:
            (D) TOPOLOGY: linear (ii) MOLECULE TYPE: peptide (xi) SEQUENCE DESCRIPTION: SEQ ID NO:11:

Lys Ala Ser Gly Gly Pro Glu
1               5

(2) INFORMATION FOR SEQ ID NO:12:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Gly Gly Gly Gly Ser
1               5

(2) INFORMATION FOR SEQ ID NO:13:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Arg Glu Asp Leu
```

NUCLEIC ACIDS ENCODING IMMUNOTOXINS CONTAINING A DISULFIDE-STABILIZED ANTIBODY FRAGMENT REPLACING HALF OR MORE OF DOMAIN IB OF PSEUDOMONAS EXOTOXIN, AND METHODS OF USE OF THE ENCODED IMMUNOTOXINS

CROSS-REFERENCE TO RELATED APPLICATIONS

This is a divisional of U.S. Ser. No. 08/809,668, filed Aug. 21, 1997, which is a national stage application of PCT/US96/16327, filed Oct. 11, 1996, which is a continuation-in-part of U.S. Ser. No. 60/005,388, filed Oct. 13, 1995. The contents of all of these applications are hereby incorporated by reference.

BACKGROUND OF THE INVENTION

This invention pertains to the production and use of Pseudomonas-derived immunotoxins modified to increase their toxicity and potency in therapy. In particular, the immunotoxins of this invention include a disulfide-stabilized (ds) target-binding agent, such as the variable region of an antibody molecule, and a Pseudomonas exotoxin that does not require proteolytic activation for cytotoxic activity.

Immunotoxins were initially produced by chemically coupling antibodies to toxins (Vitetta et al. *Cell,* 41: 653–654 (1985); Pastan et al., *Ann. Rev. Biochem.* 61: 331–354 (1992)) to form chimeric molecules. In these molecules, the antibody portion mediated selective binding to target cells, while the toxin portion mediated translocation into the cytosol and subsequent cell killing. Several toxins have been used to make immunotoxins including ricin A chain, blocked ricin, saporin, pokeweed antiviral protein, diphtheria toxin and Pseudomonas exotoxin A (PE) (Pastan et al., *Science* 254: 1173–1177 (1991); Vitetta et al., *Semin. Cell Biol.* 2: 47–58 (1991); Tazzari et al., *Br. J. Hematol* 81: 203–211 (1992); Uckun et al., *Blood,* 79: 2201–2214 (1992)).

Several clinical trials with immunotoxins have shown activity against lymphomas and other cancers derived from the hematopoietic system (Vitetta et al., *Cancer Res.* 51: 4052–4058 (1991); Grossbard et al., *J. Clin. Oncol.* 11: 726–737 (1993)). However, these immunotoxins are heterogeneous and their large size limits penetration into solid tumors. Second generation immunotoxins are totally recombinant molecules made by fusing the smallest functional module of an antibody, the Fv fragment, to a truncated toxin which lacks the cell-binding domain (Brinkmann et al., *Proc. Natl. Acad. Sci. USA* 88: 8616–8620 (1991); Kreitman et al., *Blood,* 80: 2344–2352 (1992)). The small size of single-chain Fv-immunotoxins makes them much more useful than chemical conjugates of whole antibodies for certain therapeutic applications because their small size increases tumor penetration and efficacy (Fukimori et al, *Cancer Res.* 49: 5656–5663 (1989); Jain, *Cancer Res.,* 50: 814–819 (1990); Sung et al., *Cancer Res.* 50: 7382–7392 (1990)).

Several types of recombinant Fv-immunotoxins containing PE have been made and tested in vitro as well as in animal models (Brinkmann et al., *Proc. Natl. Acad. Sci. USA* 88: 8616–8620 (1991); Kreitman et al., *Blood,* 80: 2344–2352 (1992); Batra et al., *Proc. Natl. Acad. Sci. USA* 89: 5867–5871 (1992); Reiter et al., *Cancer Res.* 54: 2714–2718 (1994); Brinkmann et al, *Proc. Natl. Acad. Sci. USA* 90: 547–551 (1993)). Initially, the Fv regions of the immunotoxins were arranged in a single-chain form (scFv-immunotoxin) with the $V_H$ and $V_L$ domains connected by a linking peptide. More recently, disulfide-stabilized forms of Fv-immunotoxins (dsFv-immunotoxins) have been generated in which the $V_H$ and $V_L$ domains are connected by a disulfide bond engineered into the framework region (see, e.g. copending application U.S. Ser. No. 08/077,252 filed on Jun. 14, 1993; Brinkmann et al., *Proc. Natl. Acad. Sci. USA* 90: 7538–7542 (1993); Reiter et al., *Protein Eng.,* 7: 697–704 (1994)). Disulfide-stabilized Fv immunotoxins are much more stable than single-chain immunotoxins and can show improved binding to antigen (Reiter et al., *J. Biol. Chem.* 269: 18327–18331 (1994); Reiter et al., *Protein Eng.* 7: 697–704 (1994)). In addition, dsfv-immunotoxins are slightly smaller in size than scfv-immunotoxins, and may exhibit better tumor penetration.

Recombinant immunotoxins containing PE must be proteolytically activated within the cell by cleavage in domain f between amino acids 279 and 280 (Ogata et al *J. Biol Chem.,* 267: 25369–25401 (1992)). To eliminate the need for intracellular proteolytic activation and thereby increase cytotoxic activity, the toxin moiety of recombinant toxins has been modified. This was initially done with recombinant toxins containing TGFα by producing a truncated toxin (PE280-613) with TGFα inserted near the end of domain III at position 607 (Theuer et al, *J. Urol.,* 149: 1626–1632 (1993); Theuer et al., *Cancer Res.,* 53: 340–347 (1993)). Because the toxin begins at position 280, it does not need proteolytic activation within the cell (Ogata et al. *J. Biol. Chem.,* 267: 25369–25401 (1992); Theuer et al. *J. Biol. Chem.,* 267: 16872–16877 (1992)). In addition, these molecules had two other mutations. One was a deletion of unnecessary residues in domain Ib (365–380). The other was to change the carboxyl terminus from REDLK (SEQ ID NO:8) to KDEL (SEQ ID NO:9) to increase cytotoxic activity (Seetharam et al. *J. Biol. Chem.,* 266: 17376–17381 (1991)). This molecule termed PE35/TGFαKDEL was 10–700 fold more active than TGFα-PE40 on several human bladder cancer cell lines (Theuer et al, *J. Urol.,* 149: 1626–1632 (1993)). However, even more specific and reactive immunotoxins are desired.

SUMMARY OF THE INVENTION

The present invention is premised, in part, on the discovery that immunotoxins comprising both a disulfide-stabilized binding agent and a Pseudomonas exotoxin modified so that proteolytic cleavage is not required for cytotoxicity, show cytotoxicity far greater than would be expected based on the performance of fusion proteins comprising either the disulfide stabilized binding protein or the modified Pseudomonas exotoxin alone.

Thus, in one embodiment, this invention provides for an immunotoxin comprising a Pseudomonas exotoxin (PE) that does not require proteolytic activation for cytotoxic activity attached to a variable heavy ($V_H$) region of an Fv antibody fragment where the variable heavy region is bound through at least one disulfide bond to a variable light ($V_L$) chain region. In a preferred embodiment, the Pseudomonas exotoxin is a truncated Pseudomonas exotoxin lacking domain Ia. In another embodiment, Pseudomonas exotoxin lacks residues 1 through 279. The variable heavy chain region can substantially replace domain Ib of the Pseudomonas exotoxin, or alternatively, it can be located in the carboxyl terminus of the Pseudomonas exotoxin. The amino terminus of the heavy chain region can be attached to the PE through a peptide linker (e.g. SGGGGS; SEQ ID NO:10). The carboxyl terminus of the heavy chain region can also be attached to the PE through a peptide linker (e.g., KASG- GPE; SEQ ID NO:11). In a preferred embodiment, the antibody fragment is from B1, B3, B5, e23, BR96, anti-Tac, RFB4, or HB21, more preferably from B1, B3, B5, and e23. The carboxyl terminal sequence of the immunotoxin can be KDEL (SEQ ID NO:9). Particularly preferred immunotoxins include PE35/e23(dsfv)KDEL and B1 (dsFv)PE33.

In another embodiment, the variable light ($V_L$) region rather than the variable heavy region ($V_H$) is attached (fused) to the Pseudomonas exotoxin, while the variable heavy ($V_H$) chain is bound to the variable light ($V_L$) chain through at least one disulfide bond. Particularly preferred embodiments include all of the embodiments described above differing only in that the $V_L$ chain is substituted for the $V_H$ chain and vice versa.

This invention also provides for nucleic acids encoding all of the above-described immunotoxins. Thus, in one embodiment, this invention provides for a nucleic acid encoding an immunotoxin comprising a heavy chain variable region of an Fv antibody fragment attached to a Pseudomonas exotoxin that does not require proteolytic activation for cytotoxic activity. The encoded heavy chain variable region contains cysteine residues that form disulfide linkages with a variable light chain region of an Fv fragment and the antibody fragments comprise the variable light or variable heavy chains of B1, B3, B5, e23, BR96, anti-Tac, RFB4, or HB21. In a preferred embodiment, the nucleic acid encodes an immunotoxin in which the heavy chain variable region is substituted for domain Ib of the Pseudomonas exotoxin. In another embodiment, the nucleic acid encodes an immunotoxin in which the heavy chain variable region is located after residue 607 of the Pseudomonas exotoxin. The PE component of the encoded immunotoxin preferably lacks amino acid residues 1 through 279. In another preferred embodiment, this invention also provides for nucleic acids as described above encoding immunotoxins in which the $V_L$ chain is substituted for the $V_H$ chain and vice versa.

It was also a discovery of this invention that single chain immunotoxins comprising $V_L$ or $V_H$ regions alone, rather than as components of Fv fragments, are capable of binding their target molecules. Thus, in yet another embodiment, this invention provides for a single chain immunotoxin fusion protein comprising a Pseudomonas exotoxin (PE) that does not require proteolytic activation for cytotoxic activity attached to a variable light ($V_L$) or a variable heavy ($V_H$) chain region. Suitable toxin components include any of the Pseudomonas exotoxins described above. In a preferred embodiment, the Pseudomonas exotoxin is a truncated Pseudomonas exotoxin lacking domain Ia. In another preferred embodiment, the Pseudomonas exotoxin lacks residues 1 through 279. The variable heavy or light chain can substantially replace domain Ib, or can be located in the carboxyl terminus of the Pseudomonas exotoxin. The amino terminus of the variable heavy or light chain region can be attached to the PE through a peptide linker (e.g., SGGGGS) while the carboxyl terminus of the variable heavy or light chain region can be attached to the PE through a peptide linker (e.g., KASGGPE). The variable heavy or light chain are preferably derived from B1, B3, B5, e23, BR96, anti-Tac, RFB4, or HB21, and more preferably from Bi, B3, B5 and e23. The immunotoxin can have the carboxyl terminal sequence KDEL.

In another embodiment, this invention provides for nucleic acids encoding any of the above-described single chain immunotoxin fusion proteins.

This invention also provides for methods of killing cells bearing a characteristic marker. The methods comprise contacting the cells with any of the above-described immunotoxins comprising a Pseudomonas exotoxin (PE) that does not require proteolytic activation for cytotoxic activity attached to a heavy chain region of an Fv antibody fragment which is bound through at least one disulfide bond to a variable light chain region or, conversely, attached to a light chain region of an Fv antibody fragment which is bound through at least one disulfide bond to a variable heavy chain region.

The immunotoxins of this invention are suitable for use in pharmacological compositions. This invention thus provides for a pharmaceutical composition comprising an effective amount of an immunotoxin in a pharmacologically acceptable excipient. Preferred immunotoxins include any of the above-described immunotoxins comprising a Pseudomonas exotoxin (PE) that does not require proteolytic activation for cytotoxic activity attached to a heavy chain region of an Fv antibody fragment which is bound through at least one disulfide bond to a variable light chain region or, conversely, attached to a light chain region of an Fv antibody fragment which is bound through at least one disulfide bond to a variable heavy chain region.

Finally, this invention also provides methods of delivering an antibody to the cytosol of a cell. The methods involve contacting the cell with a chimeric molecule comprising the antibody attached to a Pseudomonas exotoxin that does not require proteolytic cleavage for translocation into the cytosol of said cell. The chimeric molecule is preferably a fusion protein in which the antibody (e.g., a $V_H$ or a $V_L$ region) is substituted into domain Ib, domain II or the carboxyl terminus of domain III. Domain III is preferably inactivated (its cytotoxic activity substantially eliminated) by truncation, mutation, or insertion of a heterologous peptide sequence.

DEFINITIONS

Abbreviations for the twenty naturally occurring amino acids follow conventional usage (*Immunology—A Synthesis*, (2nd ed., E. S. Golub and D. R. Gren, eds., Sinauer Associates, Sunderland, Mass., 1991). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the left-hand direction is the amino-terminal direction and the right-hand direction is the carboxy-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acid" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The phrase "specifically binds to a protein" or "specifically immunoreactive with", when referring to an antibody or a "binding agent" refers to a binding reaction which is determinative of the presence of the target molecule (e.g. protein) in the presence of a heterogeneous population of proteins and other biologics. Thus, under designated immunoassay conditions, the specified binding agents or fusion proteins comprising the specified binding agents bind to a particular protein, or other target molecule, and do not bind in a significant amount to other proteins present in the sample. Specific binding to a protein under such conditions may require a binding agent that is selected for its specificity for a particular target molecule. For example, antibodies B1, B3, B5 and BR96 bind the Lewis$^Y$ carbohydrate antigen and not to any other target molecules present in a biological sample. A variety of immunoassay formats may be used to select binding agents specifically reactive with a particular target molecule. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

"Peptides" and "polypeptides" are chains of amino acids whose α carbons are linked through peptide bonds formed by a condensation reaction between the à carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group.

Typically, amino acids comprising a polypeptide are numbered in order, increasing from the amino terminal to the carboxy terminal of the polypeptide. Thus when one amino acid is said to "follow" another, that amino acid is positioned closer to the carboxy terminal of the polypeptide then the "preceding" amino acid.

The term "residue" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" refers to a characteristic region of a polypeptide. The domain may be characterized by a particular structural feature such as an alpha helix, or a β pleated sheet, by characteristic constituent amino acids (e.g. Predominantly hydrophobic or hydrophilic amino acids, or repeating amino acid sequences), or by its localization in a particular region of the folded three dimensional polypeptide. A domain may be composed of a series of contiguous amino acids or by amino acid sequences separated from each other in the chain, but brought into proximity by the folding of the polypeptide.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

A "spacer" or "linker" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "target molecule", as used herein, refers to a molecule to which the binding agent specifically binds. Typically target molecules are characteristic of a particular cell type or physiological state. Thus, for example, target molecules such as Lewis$^Y$ antigen or c-erbB2 are typically found on various cancer cells. Binding agents directed to these target molecules thus direct the immunotoxins to the cells bearing the target molecules.

BRIEF DESCRIPTION OF THE DRAWINGS

FIG. 1 provides a schematic representation of B1 immunotoxins having a disulfide-stabilized binding agent placed at the amino terminus or inserted in place of domain Ib. Positions of amino acids that span PE sequences are numbered. The arrow sign marks the proteolytic site of PE for activation. S—S shows the disulfide bond linkage between the Fv fragments. L: peptide linker; $V_H$: variable heavy chain; $V_L$: variable light chain; II: PE domain II for translocation; Ib: PE domain Ib (function unknown); III: PE domain III for ADP-ribosylation of EF2.

DETAILED DESCRIPTION

Figure 2:
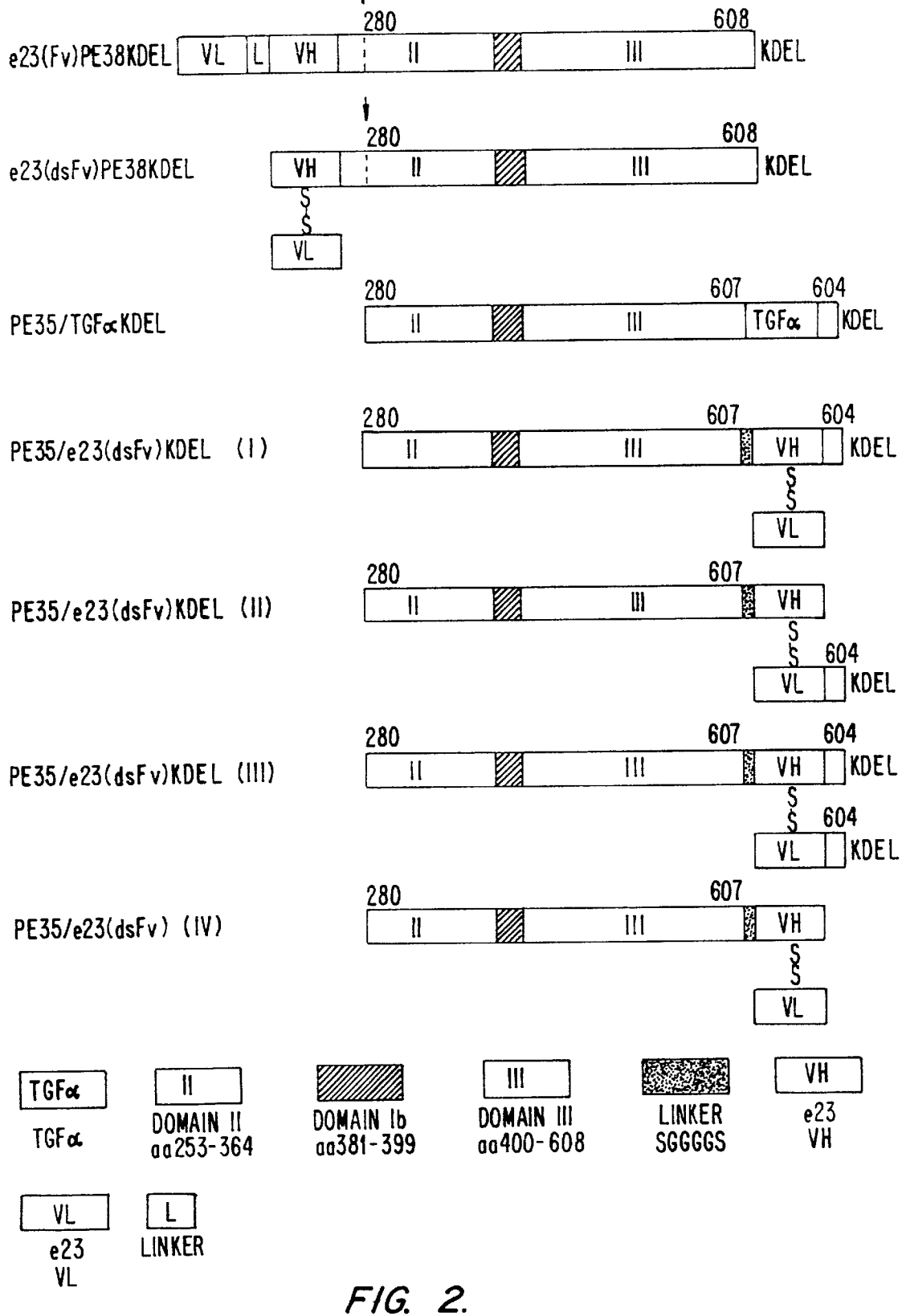
FIG. 2 provides a schematic representation of e23 immunotoxins having a carboxyl disulfide-stabilized binding agent. Position of the amino acids that span PE sequences are numbered. The amino acids listed in the one-letter code are the C-terminal residues (KDEL=SEQ ID NO:9). The arrow sign marks the proteolytic site of PE for activation. S—S shows the disulfide bond linkage between the Fv fragments Linker SGGGGS=SEQ ID NO:10.

This invention relates to Pseudomonas exotoxin (PE) based immunotoxins having increased cytotoxic activity. It was a surprising discovery of the present invention that immunotoxins comprising a disulfide-stabilized binding agent attached to a Pseudomonas exotoxin that has been modified so that proteolytic cleavage is not required for cytotoxic activity show unexpected high levels of cytotoxicity, particularly greater than a ten-fold increase in cytotoxicity to target cells. This cytotoxicity combined with the smaller size of the immunotoxin which provides greater penetration into solid tumors results in an immunotoxin of improved pharmacological efficacy. The term binding agent, as used herein, refers to a molecule that specifically recognizes and binds to a particular preselected target molecule. The binding agent is thus capable of specifically targeting cells that express preselected target molecule. Thus chimeric immunotoxins including a binding agent specifically bind to and kill or inhibit growth of cells bearing target molecules recognized by the binding agent.

Preferred binding agents are immunoglobulins, members of the immunoglobulin family or molecules derived from immunoglobulins or members of the immunoglobulin family as described below in Section II(A). Particularly preferred binding agents include immunoglobulin fragments incorporating recognition domains of the immunoglobulin (or immunoglobulin family) molecules (e.g. incorporating the variable region of an antibody).

Preferred binding agents include at least two different polypeptides that are joined together by a linker, most preferably by a disulfide linkage (e.g. formed between respective cysteines in each chain). Binding agents comprising two polypeptide chains joined by a disulfide linkage have a reduced tendency to aggregate, show a generally longer serum half-life and are said to be "stabilized". Thus a disulfide-stabilized binding agent, as used herein, refers to a binding agent comprising at least two polypeptides joined by at least one disulfide linkage. The disulfide linkage, however, need not be the only linkage joining the polypeptides. Thus, for example, a variable light and variable heavy chain of an antibody may be joined by a disulfide linkage and additionally joined by terminal peptide linker. Such a molecule may thus be expressed as a single chain fusion protein (e.g. $V_H$-peptide-$V_L$) where the $V_H$ and $V_L$ polypeptides are subsequently cross-inked by the formation of a disulfide linkage. Methods of producing disulfide-stabilized binding agents can be found in copending patent application U.S. Ser. No. 08/077,252, filed on Jun. 14, 1993.

As indicated above, the disulfide-stabilized binding agent is attached to a Pseudomonas exotoxin which is modified so that it is cytotoxic without requiring proteolytic activation. As explained below in Section III, this typically entails truncating the amino terminus to at least position 279. Methods of producing Pseudomonas exotoxins that do not require proteolytic cleavage for activation are described in copending patent application Ser. No. 08/405,615, filed on Mar. 15, 1995 which is a continuation of Ser. No. 07/901,709 filed on Jun. 18, 1992.

The disulfide-stabilized binding agent may be located at virtually any position within the modified Pseudomonas exotoxin. In one preferred embodiment, the binding agent is inserted in replacement for domain Ia as has been accomplished in what is known as the TGFα/PE40 molecule (also referred to as TP40) described in Heimbrook et al., *Proc. Natl. Acad. Sci., USA*, 87: 4697–4701 (1990) and in commonly assigned U.S. Ser. No. 07/865,722 filed Apr. 8, 1992 and in U.S. Ser. No. 07/522,563 filed May 14, 1990.

The disulfide-stabilized binding agent may additionally substitute for all of domain Ib or portions of it. Thus, for example residues 343 through 394 in domain Ib may be eliminated or replaced with one of the two chains of the disulfide-stabilized binding agent.

The disulfide-stabilized binding agent may alternatively be located near or at the amino or carboxyl terminus. Where the disulfide-stabilized binding agent is located in the carboxyl terminus, it is preferably located after amino acid 604, with a position between amino acid 604 and 608 being more preferred and a position after about amino acid 607 being most preferred. An appropriate carboxyl end of PE can be recreated by placing amino acids about 604–613 of PE after the binding agent. Thus, the disulfide-stabilized binding agent is preferably inserted within the recombinant PE molecule after about amino acid 607 and is followed by amino acids 604–613 of domain III of PE. The new carboxyl terminus can also include the endoplasmic retention sequences REDLK (SEQ ID NO:8) and KDEL (SEQ ID NO:9), with KDEL (SEQ ID NO:9) being most preferred. The terminus may also include terminal PE amino acids. Thus, in one particularly preferred embodiment, the disulfide-stabilized binding agent is an antibody which is located after residue 607 and then followed by PE residues 604–608 which, in turn, are followed by KDEL (SEQ ID NO:9). The $V_L$ or $V_H$ regions from a desired antibody may also be inserted in a single chain form within domain III.

Where the disulfide-stabilized binding agent is an antibody, more particularly a Fv region of an antibody, the modified PE can be fused to either the $V_H$ or the $V_L$ domain of the Fv in any of the PE regions as described above. The fusion between the PE and the $V_L$ or $V_H$ can be direct or through one or more peptide linker(s). Such linkers can be attached to the $V_H$ or the $V_L$ at either the carboxyl terminal of the variable chain, the amino terminal of the variable chain, or at both termini.

When the variable heavy ($V_H$) chain is fused to the PE, the variable light ($V_L$) chain is joined to the fused variable heavy chain by one or more disulfide linkages. Conversely, when the variable light ($V_L$) chain is fused to the PE, the variable heavy ($V_H$) chain is joined to the fused variable light chain by one or more disulfide linkages.

It was also a discovery of the present invention that variable heavy or light chain regions alone, rather than as a component of an Fv region, are capable of specifically binding to their target molecules. Thus, in one embodiment, this invention provides for single chain immunotoxin fusion proteins comprising a Pseudomonas exotoxin (PE) that does not require proteolytic activation for cytotoxic activity attached to a variable light ($V_L$) or a variable heavy ($V_H$) chain region. In effect these fusion proteins are made in the same manner as the disulfide-stabilized fusion proteins described above, but the step whereby the respective variable regions are joined by disulfide linkages is omitted. In addition, as no disulfide linkages need be formed, there is no need to introduce cysteine into either of the variable regions, or to eliminate cysteines existing in the PE. Either the variable light chain or the variable heavy chain can be expressed in fusion with the modified PE.

Those skilled in the art will realize that additional modifications, deletions, insertions and the like may be made to the disulfide-stabilized binding agent and PE genes. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. Typical modifications, include, but are not limited to introduction of an upstream methionine for transcription initiation, mutation of residues to cysteine in the $V_H$ or $V_L$ regions for the creation of disulfide linkages, mutation of cysteine at position 287 in PE to serine to prevent unwanted disulfide linkage formation, an upstream (amino) peptide linker (e.g. GGGGS; SEQ ID NO:12), a downstream (carboxyl) peptide linker (e.g. KASGGPE; SEQ ID NO:11), and so forth. All such constructions may be made by methods of genetic engineering well known to those skilled in the art (see, generally, Berger and Kimmel, *Guide to Molecular Cloning Techniques, Methods in Enzymology Volume* 152 Academic Press, Inc., San Diego, Calif. (Berger); Sambrook et al. *Molecular Cloning—A Laboratory Manual*(2nd ed.) Vol. 1–3, Cold Spring Harbor Laboratory, Cold Spring Harbor Press, NY, (1989); and *Current Protocols in Molecular Biology,* F. M. Ausubel et al., eds., a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. *Proc. Nat'l Acad. Sci. USA,* 86: 10029–10033 (1989)).

I. Disulfide Stabilized Binding Protein

A) General immunoglobulin structure.

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$. (See, generally, Davies et al. *Ann. Rev. Biochem.,* 59: 439–473 (1990)).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD or about 214 amino acids) and one "heavy" chain (about 50–70 kD or about 446 amino acids). The C-terminus of each chain defines a constant region (C) that determines the antibody's effector function (e.g., complement fixation, opsonization, etc.), while the N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Members of the immunoglobulin family all share an immunoglobulin-like domain characterized by a centrally placed disulfide bridge that stabilizes a series of antiparallel β strands into an immunoglobulin-like fold. Members of the family (e.g., MHC class I, class II molecules, antibodies and T cell receptors) can share homology with either immunoglobulin variable or constant domains.

Full-length immunoglobulin or antibody "light chains" (generally about 25 kilodaltons (Kd), about 214 amino acids) are encoded by a variable region gene at the N-terminus (generally about 110 amino acids) and a constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes (encoding about 330 amino acids). Typically, the "$V_L$" will include the portion of the light chain encoded by the $V_L$ and $J_L$ (J or joining region) gene segments, and the "$V_H$" will include the portion of the heavy chain encoded by the $V_H$, and DH (D or diversity region) and $J_H$ gene segments. See generally, Roitt, et al., *Immunology,* Chapter 6, (2d ed. 1989) and Paul, *Fundamental Immunology;* Raven Press (2d ed. 1989). The Fv antibody fragment includes the variable heavy chain and variable light chain regions.

An immunoglobulin light or heavy chain variable region comprises three hypervariable regions, also called complementarity determining regions or CDRs, flanked by four relatively conserved framework regions or FRs. Numerous framework regions and CDRs have been described (see, Kabat et al., *Sequences of Proteins of Immunological Interest,* U.S. Government Printing Office, NIH Publication No. 91-3242 (1991); referred to herein as "Kabat and Wu"). The sequences of the framework regions of different light or heavy chains are relatively conserved. The CDR and FR polypeptide segments are designated empirically based on sequence analysis of the Fv region of preexisting antibodies or of the DNA encoding them. From alignment of antibody sequences of interest with those published in Kabat and Wu and elsewhere, framework regions and CDRs can be determined for the antibody or other ligand binding moiety of interest. The combined framework regions of the constituent light and heavy chains serve to position and align the CDRs. The CDRs are primarily responsible for binding to an epitope of an antigen and are typically referred to as CDR1, CDR2, and CDR3, numbered sequentially starting from the N-terminus of the variable region chain. Framework regions are similarly numbered.

The general arrangement of T cell receptor genes is similar to that of antibody heavy chains, T cell receptors (TCR) have both variable domains (V) and constant (C) domains. The V domains function to bind antigen. There are regions in the V domain homologous to the framework CDR regions of antibodies. Homology to the immunoglobulin V regions can be determined by alignment. The V region of the TCRs has a high amino acid sequence homology with the Fv of antibodies. Hedrick et al, *Nature* (London) 308:153–158 (1984)).

The term CDR, as used herein, refers to amino acid sequences which together define the binding affinity and specificity of the natural variable binding region of a native immunoglobulin binding site (such as Fv), a T cell receptor (such as $V_\alpha$ and $V_\beta$), or a synthetic polypeptide which mimics this function. The term "framework region" or "FR", as used herein, refers to amino acid sequences interposed between CDRs.

The "binding agents" referred to here are those molecules that have a variable domain that is capable of functioning to bind specifically or otherwise recognize a particular ligand or antigen. Moieties of particular interest include antibodies and T cell receptors, as well as synthetic or recombinant binding fragments of those such as Fv, Fab, F(ab')$_2$ and the like. Appropriate variable regions include $V_H$, $V_L$, $V_\alpha$, and $V_\beta$ and the like.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to braak the disulfide linkage in the hinge region thereby converting the (Fab')$_2$ dimer into an Fab' monomer. The Fab' monomer is essentially an Fab with part of the hinge region. The Fv region is the variable part of Fab; a $V_H$-$V_L$ dimer (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such fragments (e.g., Fv) may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include disulfide-stabilized antibodies, more preferably disulfide-stabilized Fv (dsfv) antibodies in which a variable heavy and a variable light chain are joined together by at least one disulfide linkage to form an intact Fv fragment.

Practice of this invention preferably employs the Fv portions of an antibody or the V portions of a TCR. Other sections, e.g., $C_H$ and $C_L$, of native immunoglobulin protein structure need not be present and normally are intentionally omitted from the polypeptides of this invention. However, the polypeptides of the invention may comprise additional polypeptide regions defining a bioactive region, e.g., a toxin or enzyme, or a site onto which a toxin or a remotely detectable substance can be attached, as will be described below.

B) Preparation of Fv Fragments

Information regarding the Fv antibody fragments or other ligand binding moiety of interest is required in order to produce proper placement of the disulfide bond to stabilize the desired disulfide stabilized fragment, such as an Fv fragment (dsFv). The amino acid sequences of the variable fragments that are of interest are compared by alignment with those analogous sequences in the well-known publication by Kabat and Wu, supra, to determine which sequences can be mutated so that cysteine is encoded for in the proper position of each heavy and light chain variable region to provide a disulfide bond in the framework regions of the desired polypeptide fragment. Cysteine residues are preferred to provide the covalent disulfide bonds. For example, a disulfide bond could be placed to connect FR4 of $V_L$ and FR2 of $V_H$; or to connect FR2 of $V_L$ and FR4 of $V_H$.

After the sequences are aligned, the amino acid positions in the sequence of interest that align with the following positions in the numbering system used by Kabat and Wu are identified: positions 43, 44, 45, 46, and 47 (group 1) and positions 103, 104, 105, and 106 (group 2) of the heavy chain variable region; and positions 42, 43, 44, 45, and 46 (group 3) and positions 98, 99, 100, and 101 (group 4) of the light chain variable region. In some cases, some of these positions may be missing, representing a gap in the alignment.

Then, the nucleic acid sequences encoding the amino acids at two of these identified positions are changed such that these two amino acids are mutated to cysteine residues. The pair of amino acids to be selected are, in order of decreasing preference:

$V_H44$-$V_L105$
$V_H44$-$V_L99$
$V_H44$-$V_L100$,
$V_H105$-$V_L43$,
$V_H105$-$V_L42$,
$V_H44$-$V_L101$,
$V_H10$-$V_L43$,
$V_H104$-$V_L43$,
$V_H45$-$V_L98$,
$V_H46$-$V_L98$,
$V_H103$-$V_L43$,
$V_H103$-$V_L44$,
$V_H103$-$V_L45$.

Most preferably, substitutions of cysteine are made at the positions:

$V_H44$-$V_L105$ (see, e.g., B1(dsfv)-PE33);
$V_H44$-$V_L99$ (see, e.g., PE35/e23(dsFv)KDEL);
$V_H44$-$V_L100$; or
$V_H105$-$V_L43$.

(The notation $V_H44$-$V_L100$, for example, refers to a polypeptide with a $V_H$ having a cysteine at position 44 and a cysteine in $V_L$ at position 100; the positions being in accordance with the numbering given by Kabat and Wu.)

Note that with the assignment of positions according to Kabat and Wu, the numbering of positions refers to defined conserved residues and not to actual amino acid positions in a given antibody. For example, CysL100 (of Kabat and Wu) which is used to generate ds(Fv)B3 as described in the example below, actually corresponds to position 105 of B3($V_L$).

In the case of $V_\alpha$ and $V_\beta$ of T cell receptors, reference can also be made to the numbering scheme in Kabat and Wu for T cell receptors. Substitutions of cysteines can be made at position 41, 42, 43, 44 or 45 of $V_\alpha$ and at position 106, 107, 108, 109 or 110 of $V_\beta$; or at position 104, 105, 106, 107, 108 or 109 of $V_\alpha$ and at position 41, 42, 43, 44 or 45 of $V_\beta$, such positions being in accordance with the Kabat and Wu numbering scheme for TCRs. When such reference is made, the most preferred cysteine substitutions are $V_\alpha42$-$V_\beta110$ and $V_\alpha108$-$V_\beta42$. $V_\alpha$ positions 106, 107 and $V_\beta$ positions 104, 105 are CDR positions, but they are positions in which disulfide bonds can be stably located.

As an alternative to identifying the amino acid position for cysteine substitution with reference to the Kabat and Wu numbering scheme, one could align a sequence of interest with the sequence for monoclonal antibody (MAb) B1, B3, or B5 hybridomas of which have all been deposited with the American Type Culture Collection in Rockville, Md. with designations of HB 10569, HB 10572, and HB 10573) as described in U.S. Pat. No. 5,242,813, copending application U.S. Ser. No. 07/767,331 filed on Sep. 30, 1991, copending application U.S. Ser. No. 08/051,133, filed on Apr. 22, 1993, copending applications U.S. Ser. No. 08/331,391, 08/331,397 and 08/331,396, all filed on Oct. 28, 1994, and by Benhar et al., *Clin. Cancer. Res.*, 1: 1023–1029 (1995). The amino acid positions of B3 which correlate with the Kabat and Wu $V_H$ positions set forth above for Group 1 are 43, 44, 45, 46, and 47, respectively; for Group 2 are 109, 110, 111, and 112, respectively. The amino acid positions of B3 which correlate with the Kabat and Wu $V_L$ positions set forth above for Group 3 are 47, 48, 49, 50 and 51, respectively; Group 4 are 103, 104, 105, and 106, respectively.

Alternatively, the sites of mutation to the cysteine residues can be identified by review of either the actual antibody or the model antibody of interest as exemplified below. Computer programs to create models of proteins such as antibodies are generally available and well-known to those skilled in the art (see Kabat and Wu; Loew, et al., *Int. J. Quant. Chem., Quant. Biol Symp.*, 15:55–66 (1988); Bruccoleri, et al., *Nature*, 335:564–568 (1988); and Chothia, et al., *Science*, 233:755–758 (1986)). Commercially available computer programs can be used to display these models on a computer monitor, to calculate the distance between atoms, and to estimate the likelihood of different amino acids interacting (see, Ferrin, et al., *J. Mol. Graphics*, 6: 13–27 (1988)). For example, computer models can predict charged amino acid residues that are accessible and relevant in binding and then conformationaly restricted organic molecules can be synthesized. See, for example, Saragovi, et al., *Science*, 253:792 (1991). In other cases, an experimentally determined actual structure of the antibody may be available.

A pair of suitable amino acid residues should (1) have a $C_\alpha$-$C_\alpha$ distance between the two residues less than or equal to 8 Å, preferably less than or equal to 6.5 Å (determined from the crystal structure of antibodies which are available such as those from the Brookhaven Protein Data Bank) and (2) be as far away from the CDR region as possible. Once they are identified, they can be substituted with cysteines. The $C_\alpha$-$C_\alpha$ distances between residue pairs in the modeled B3 at positions homologous to those listed above are set out in Table 1, below.

Introduction of one pair of cysteine substitutions will be sufficient for most applications. Additional substitutions may be useful and desirable in some cases.

Modifications of the genes to encode cysteine at the target point may be readily accomplished by well-known techniques, such as site-directed mutagenesis (see, Gillian and Smith, *Gene*, 8: 81–97 (1979) and Roberts, et al, *Nature*, 328:731–734 (1987)) by the method described in Kunkel, *Proc. Natl. Acad. Sci. USA* 82:488–492 (1985), or by any other means known in the art.

Separate vectors with sequences for the desired $V_H$ and $V_L$ sequences (or other homologous V sequences) may be made from the mutagenized plasmid. The sequences encoding the heavy chain regions and the light chain regions are produced and expressed in separate cultures in any manner known or described in the art, with the exception of the guidelines provided below. If another sequence, such as a sequence for a toxin, is to be incorporated into the expressed polypeptide, it can be linked to the $V_H$ or the $V_L$ sequence at either the N- or C-terminus or be inserted into other protein sequences in a suitable position. For example, for *Pseudomonas exotoxin* (PE) derived fusion proteins, either $V_H$ or $V_L$ should be linked to the N-terminus of the toxin or be inserted into domain III of PE, like for example TGFα in Theuer et al., *J. Urol.*, 149: 1626–1632 (1993), or inserted in place of domain Ib of PE. For Diphtheria toxin-derived immunotoxins, $V_H$ or $V_L$ is preferably linked to the C-terminus of the toxin.

Peptide linkers, such as those used in the expression of recombinant single chain antibodies, may be employed to link the two variable regions ($V_H$ and $V_L$, $V_{and\ V\beta}$) if desired and may positively increase stability in some molecules. Bivalent or multivalent disulfide stabilized polypeptides of the invention can be constructed by connecting two or more, preferably identical, $V_H$ regions with a peptide linker and adding $V_L$ as described in the examples, below. Connecting two or more $V_H$ regions by linkers is preferred to connecting $V_L$ regions by linkers since the tendency to form homodimers is greater with $V_L$ regions. Peptide linkers and their use are well-known in the art. See, e.g., Huston et al., *Proc. Natl. Acad. Sci. USA*, supra; Bird et al., *Science*, supra; Glockshuber et al., supra; U.S. Pat. No. 4,946,778, U.S. Pat. No. 5,132,405 and most recently in Stemmer et al., *Biotechniques* 14:256–265 (1993).

C) Various dsFv fragment molecules.

It should be understood that the description of the dsFv peptides described above can cover all classes/groups of antibodies of all different species (e.g., mouse, rabbit, goat, human) chimeric peptides, humanized antibodies and the like. "Chimeric antibodies" or "chimeric peptides" refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, chimeric antibodies can include antibodies where the framework and complementarity determining regions are from different sources. For example, non-human CDRs are integrated into human framework regions linked to a human constant region to make "humanized antibodies." See, for example, PCT Application Publication No. WO 87/02671, U.S. Pat. No. 4,816,567, EP Patent Application 0173494, Jones, et al., *Nature*, 321:522–525 (1986) and Verhoeyen, et al., *Science*, 239:1534–1536 (1988). Similarly, the source of $V_H$ can differ from the source of $V_L$.

Particularly preferred binding agents are derived from antibodies that specifically recognize and bind to receptors or other surface markers characteristic of cancer cells. Such markers, and corresponding antibodies are well known to those of skill and include, but are not limited to carcinoembryonic antigen (CEA), the transferrin receptor (targeted by HB21), the EGF receptor (targeted by TGFα), P-glycoprotein, c-erbB2 (targeted by e23), Lewis$^Y$ carbohydrate antigens (targeted by B1, B3, B5, BR96, etc.), the IL-2 receptor (targeted by anti-Tac), and antigens described in the Abstracts of the Third International Conference on Monoclonal Antibody Immunoconjugates for Cancer (San Diego, Calif. 1988).

D) Molecules homologous to antibody Fv domains—T-cell receptors.

This binding agents used in this invention can be derived from molecules that exhibit a high degree of homology to the antibody Fv domains, including the ligand-specific V-region of the T-cell receptor (TCR). An example of such an application is outlined below. The sequence of the antigen-specific V region of a TCR molecule, 2B4 (Becker et al, *Nature* (London) 317: 430–434 (1985)), was aligned against the Fv domains of two antibody molecules McPC603 (see below) and J539 (Protein Data Bank entry 2FBJ), using a standard sequence alignment package. When the $V_\alpha$ sequence of 2B4 was aligned to the $V_H$ sequences of the two antibodies, the S1 site residue, corresponding to $V_H 44$ of B3, can be identified as $V_\alpha 43S$ (TCR 42 in the numbering scheme of Kabat and Wu) and the S2 site residue, corresponding to $V_H 111$ of B3, as $V_\alpha 104Q$ (TCR 108 in the numbering scheme of Kabat and Wu). When the same $V_\alpha$ sequence was aligned to the $V_L$ sequences of the two antibodies, the same residues, $V_\alpha 43S$ and $V_\alpha 104Q$, can be identified, this time aligned to the residues corresponding to $V_L 48$ and $V_L 105$ of B3, respectively. Similarly, the 2B4 residues $V_\beta 42E$ and $V\beta 107P$ (TCR 42 and 110 in the numbering scheme of Kabat, et al.) can be aligned to antibody residues corresponding to $V_H 44$ and $V_H 111$ of B3 and at the same time to $V_L 48$ and $V_L 105$ of B3. Therefore, the two most preferred interchain disulfide bond sites in this TCR are $V_\alpha 43$ - $V_\beta 107$ and $V_\alpha 104$ - $V_\beta 42$. Mutating the two residues in one of these pairs of residues into cysteine will introduce a disulfide bond between the $\alpha$ and $\beta$ chains of this molecule. The stabilization that results from this disulfide bond will make it possible to isolate and purify these molecules in large quantities.

II. Modified Toxins

As indicated above, the preferred immunotoxins comprise a disulfide-stabilized binding agent joined to a Pseudomonas exotoxin modified (e.g. truncated) so that proteolytic cleavage is not required for cytotoxic activity. As used herein, cytotoxic activity refers to the ability to kill a cell or to significantly reduce its growth or proliferation rate.

The PE molecules of this invention are uniquely characterized by their increased cytotoxicity to target cells and increased antitumor activity when coupled with a disulfide-stabilized binding agent specific for the target cells. The increased cytotoxicity occurs in comparison to the use of native fusion proteins (comprising a PE that does require proteolytic cleavage) joined to a disulfide stabilized binding agent (see, e.g. commonly assigned U.S. Ser. No. 08/077,252, filed on Jun. 14, 1993) or in comparison to fusion proteins comprising a modified PE that does not require proteolytic activation fused to a single chain Fv (scFv) (see, e.g. commonly assigned U.S. Ser. No. 08/405,615, filed on Mar. 15, 1995).

Assays for determining cytotoxicity typically involve a comparison between the fusion protein comprising the subject PE molecule and a disulfide-stabilized binding agent and a fusion protein comprising a reference PE molecule, e.g. PB40, joined to a disulfide-stabilized binding agent or conversely a modified PE molecule joined to a single chain Fv (scFv). The respective fusion proteins are then tested in cytotoxicity assays against cells specific for the binding agent. $IC_{50}$s (defined below) obtained may be adjusted to obtain a cytotoxicity index by adjusting the values such that the concentration of toxin that displaces 50% of labeled ligand from ligand receptors is divided by the $IC_{50}$ of the recombinant toxin on cells bearing the ligand receptors. The cytotoxicity index for each PE molecule is then compared.

PE molecules having corrected cytotoxicity indices of about 20 times or more, preferably about 60 times or more, and most preferably about 300 times or more, over PE40 or other PE molecules where no deletion of domain II has occurred are desired. A PE molecule lacking domain Ia may be expressed by plasmid pJH8 which expresses domains II, Ib and III. Plasmid pJH8 is described in U.S. Pat. No. 4,892,827 and is available from the American Type Culture Collection in Rockville, Md. as ATCC 67208.

"$IC_{50}$" refers to the concentration of the toxin that inhibits protein synthesis in the target cells by 50%, which is typically measured by standard $^3H$-leucine incorporation assays. Displacement assays or competitive binding assays are well known and described in the art. They measure the ability of one peptide to compete with another peptide for the binding of a target antigen.

A preferred PE molecule is one in which domain Ia is deleted and no more than the first 27 amino acids have been deleted from the amino terminal end of domain II. This substantially represents the deletion of amino acids 1 to 279. The cytotoxic advantage created by this deletion is greatly decreased if the following deletions are made: 1–281; 1–283; 1–286; and 314–380. It is surprising that the deletion of 27, but not 29, 31, 33 or 36 amino acids from the amino end of domain II results in increased toxic activity since this domain is responsible for the translocation of the toxin into the cytosol.

In addition, the PE molecules can be further modified using site-directed mutagenesis or other techniques known in the art, to alter the molecule for particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDX (SEQ ID NO:8) (as in native PE), REDL (SEQ ID NO:13) or KDEL (SEQ ID NO:9), repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87:308–312 and Seetharam et al, *J. Biol Chem.* 266: 17376–17381 (1991) and commonly assigned, U.S. Ser. No. 07/459,635 filed January 2, 1990).

Deletions of amino acids 365–380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial.

As an alternative to deletion, domain Ib can be substituted with the disulfide stabilized binding agent as described above and in Example 1.

III. Protein Expression and Purification

The fusion proteins of this invention can be produced according to a number of means well known to those of skill in the art. Where the disulfide-stabilized binding agent and/or the modified Pseudomonas exotoxin are relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-termninal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol.* 2: *Special Methods in Peptide Synthesis, Part A.,*Merrifield, et al. *J. Am. Chem. Soc.,* 85: 2149–2156 (1963), and Stewart et al, *Solid Phase Peptide Synthesis, 2nd ed.* Pierce Chem. Co., Rockford, Ill. (1984) which are incorporated herein by reference.

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. PE35/e23(dsFv) KDEL, B1(dsFv)-PE33, etc.) of this invention may be prepared by any suitable method, including, for example, cloning and restriction of appropriate sequences or direct chemical synthesis by methods such as the phosphotriester method of Narang et al. *Meth. Enzymol* 68: 90–99 (1979); the phosphodiester method of Brown et al, *Meth. Enzwmol* 68: 109–151 (1979); the diethylphosphoramidite method of Beaucage et al., *Tetra. Lett.,* 22: 1859–1862 (1981); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, for example, in a preferred embodiment, B1($V_H$)R44C DNA was PCR amplified, using primers that create a peptide linker (GGGGS; SEQ ID NO:12) at the 5' end of $V_H$ along with a Bam HI, and another peptide linker (e.g.KASGGPE; SEQ ID NO:11) at the 3' end along with a HindIII restriction site. The resulting DNA was then used to replace domain Ib of PE37 (pDF₁) by site directed mutagenesis to make pCTK104 encoding B1($V_H$R44C)PE33.

While the two molecules are preferably essentially directly joined together, one of skill will appreciate that the molecules may be separated by a peptide spacer consisting of one or more amino acids. Generally the spacer will have no specific ibiological activity other than to join the proteins or to preserve some minimum distance or other spatial relationship between them. However, the constituent amino acids of the spacer may be selected to influence some property of the molecule such as the folding, net charge, or hydrophobicity.

Proteins of the invention can be expressed in a variety of host cells, including *E. coli*, and other bacterial hosts. The recombinant protein gene will be operably linked to appropriate expression control sequences for each host. For *E. coli* this includes a promoter such as the T7, trp, tac, lac or lambda promoters, a ribosome binding site, and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Methods for expressing polypeptides and/or refolding to an appropriate folded form, including disulfide-stabilized binding agents and immunotoxins from bacteria such as *E. coli* have been described, are well-known and are applicable to the polypeptides of this invention. See, Buchner et al., *Analytical Biochemistry* 205:263–270 (1992); Pluckthun, *Biotechnology,* 9:545 (1991); Huse, et al., *Science,* 246:1275 (1989) and Ward, et al., *Nature,* 341:544 (1989)).

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. An exemplary buffer with a reducing agent is: 0.1 M Tris, pH8, 6M guanidine, 2 mM EDTA, 0.3 M DTE (dithioerythritol). Reoxidation of protein disulfide bonds can be effectively catalyzed in the presence of low molecular weight thiol reagents in reduced and oxidized form, as described in Saxena et al., *Biochemistry* 9: 5015–5021 (1970), and especially described by Buchner, et al., *Anal. Biochem.,* supra (1992).

Renaturation is typically accomplished by dilution (e.g. 100-fold) of the denatured and reduced protein into refolding buffer. An exemplary buffer is 0.1 M Tris, pH8.0, 0.5 M L-arginine, 8 mM oxidized glutathione (GSSG), and 2 mM EDTA.

In a preferred modification to the single chain antibody protocol, the heavy and light chain regions of the disulfide-stabilized binding agent were separately solubilized and reduced and then combined in the refolding solution. A preferred yield is obtained when these two proteins are mixed in a molar ratio such that a molar excess of one protein over the other does not exceed a 5 fold excess.

It is desirable to add excess oxidized glutathione or other oxidizing low molecular weight compounds to the refolding solution after the redox-shuffling is completed. Alternatively, the final oxidation could be omitted and the refolding carried out at pH 9.5.

Once expressed, the recombinant proteins can be purified according to standard procedures of the art, including ammonium sulfate precipitation, affinity columns, column chromatography, and the like (see, generally, R. Scopes, *Protein Purification,* Springer-Verlag, N.Y. (1982) and Deutscher, M. P. *Methods in Enzymology Vol.* 182: *Guide to Protein Purification,* Academic Press, Inc. N.Y. (1990)). In a preferred embodiment, folded disulfide-stabilized and immunotoxins are purified by sequential ion exchange (Q-Sepharose and Mono Q) followed by size exclusion chromatography on a TSK G3000SW (Toso Haas) column. Substantially pure compositions of at least about 90 to 95 % homogeneity are preferred, and 98 to 99% or more homogeneity are most preferred for pharmaceutical uses. Once purified, partially or to homogeneity as desired, the polypeptides should be substantially free of endotoxin for pharmaceutical purposes and may then be used therapeutically.

IV. Binding Affinity of dsFv Polypeptides

The immunotoxins of this invention are capable of specifically binding a target molecule. For this invention, a polypeptide specifically binding a ligand generally refers to a molecule capable of reacting with or otherwise recognizing or binding a marker (e.g. antigen or receptor) on a target cell. An antibody or other polypeptide has binding affinity for a ligand or is specific for a ligand if the antibody or peptide binds or is capable of binding the ligand as measured or determined by standard antibody-antigen or ligand-receptor assays, for example, competitive assays, saturation assays, or standard immunoassays such as EUSA or RIA. This definition of specificity applies to single heavy and/or light chains, CDRs, fusion proteins or fragments of heavy and/or light chains, that are specific for the ligand if they bind the ligand alone or in combination.

In competition assays the ability of an antibody or peptide fragment to bind a target molecule is determined by detecting the ability of the peptide to compete with the binding of a compound known to the target molecule. Numerous types of competitive assays are known and are discussed herein. Alternatively, assays that measure binding of a test compound in the absence of an inhibitor may also be used. For instance, the ability of a molecule or other compound to bind the target molecule can be detected by labelling the molecule of interest directly or the molecule be unlabelled and detected indirectly using various sandwich assay formats. Numerous types of binding assays such as competitive binding assays are known (see, e.g., U.S. Pat. Nos. 3,376, 110, 4,016,043, and Harlow and Lane, *Antibodies: A Laboratory Manual*, Cold Spring Harbor Publications, N.Y. (1988)). Assays for measuring binding of a test compound to one component alone rather than using a competition assay are also available. For instance, immunoglobulin polypeptides can be used to identify the presence of the binding ligand. Standard procedures for monoclonal antibody assays, such as ELISA, may be used (see, Harlow and Lane, supra). For a review of various signal producing systems which may be used, see, U.S. Pat. No. 4,391,904.

V. Pharmaceutical Compositions

The recombinant fusion proteins and pharmaceutical compositions of this invention are particularly useful for parenteral administration, such as intravenous administration or administration into a body cavity or lumen of an organ. The compositions for administration will commonly comprise a solution of the PE molecule fusion protein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the recombinant fusion proteins of the present invention are included a variety of disease conditions caused by specific human cells that may be eliminated by the toxic action of the protein. One preferred application is the treatment of cancer, such as by the use of immunotoxins comprising disulfide-stabilized binding agents that specifically target and bind tumor markers. Such binding agents include antibodies that bind antigens (markers) found on cancer cells. Such targets are well known to those of skill in the art and include, but are not limited to carcinoembryonic antigen (CEA), the transferrin receptor (targeted by TGFα), P-glycoprotein, c-erbB2 (targeted by e23), Lewis$^Y$ carbohydrate antigens (targeted by B1, B3, B5, BR96, etc.) and antigens described in the Abstracts of the Third International Conference on Monoclonal Antibody Immunoconjugates for Cancer (San Diego, Calif. 1988).

Other applications include the treatment of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The fusion proteins may also be used in vitro, for example, in the elimination of harmful cells from bone marrow before transplant. The ligand binding agent portion of the fusion protein is chosen according to the intended use. Proteins on the membranes of T cells that may serve as targets for the binding agent include CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte antigens for the binding agent are described in *Leucocyte Typing III*, A. J. McMichael, ed., Oxford University Press, 1987.

Those skilled in the art will realize that ligand binding agents may be chosen that bind to receptors expressed on still other types of cells as described above, for example, membrane glycoproteins or growth factor or hormone receptors such as epidermal growth factor receptor and the like.

VI. Transport of Antibodies into the Cytosol

In another embodiment, this invention provides compositions and methods for transporting antibodies into the cytosol of the cell. The antibodies thus transported may be selected to bind to particular intracellular components (e.g. particular proteins in signal transduction systems, cytoskeletal elements, particular target RNAs, and the like). The bound antibodies can inhibit the normal activity of the target molecule and can thus be used to selectively "knock out" particular intracellular functions. Depending on the antibody target this may prove cytotoxic, or may simply alter the activity of the cell.

Thus, for example, in one embodiment, the antibody $V_H$ or $V_L$ may specifically bind and inhibit an RNA transcription product of an oncogene, thus preventing transformation of the target cell. Alternatively, the antibody may simply act as a label for detection of the particular intracellular component to which it binds.

Compositions for the intracellular delivery of the antibody are preferably fusion proteins formed by joining a Pseudomonas exotoxin to an antibody fragment, more preferably to a $V_H$ or a $V_L$ antibody fragment. The Pseudomonas exotoxin is preferably truncated, but still includes a functional translocation domain (domain II).

In a preferred embodiment, the antibody is located in domain II or III of the PE. Domain III, having the ADP ribosylation activity must be inactivated (e.g., by truncation, insertion of a foreign peptide sequence, or through complete elimination of domain) so that only antibody binding effects are manifested.

In a particularly preferred embodiment, the antibody variable domain, either heavy or light chain, should be located in domain II or III of a truncated PE which does not require proteolytic activation. Thus, for example, in B1($V_H$) PE33, or PE35/e23($V_H$)KDEL, the $V_H$ insert is not removed by proteolysis, but is translocated along with domain II and III of PE.

EXAMPLES

The following examples are offered to illustrate, but not to limit the present invention.

Example 1

Preparation and Testing of B1(dsFv)-PE33

Monoclonal antibody (MAb) B1 is a murine antibody directed against Lewis$^Y$(Le$^Y$) and related carbohydrate antigens which are abundant on the surface of many carcinomas (Pastan et al., *Cancer Res.* 51, 3781–3787 (1991)). MAb B1 has been used to make both single-chain and disulfide-stabilized Fv immunotoxins (Pastan et al., *Cancer Res.* 51, 3781–3787 (1991), Benhar, et al., *Prot. Eng.,* 7: 1509–1515 (1995), and Benhar et al. *Clin. Cancer. Res.,* 1: 1023–1029 (1995)). These agents are capable of causing complete regressions of established xenografts in nude mice.

To achieve the goal of developing a recombinant immunotoxin that is small, stable and does not need proteolytic processing, domain Ib (amino acids 365–394) of PE37 (a truncated form of PE [residues 280 through 613] that only contains the portion of the toxin that undergoes translocation to the cytosol) was replaced with the $V_H$ fragment of MAb B1 linked to the $V_L$ domain with a disulfide bond (FIG. 1). As illustrated herein, the resulting molecule, B1(dsFv)-PE33 is more active than any previous MAb B1 containing immunotoxins.

A) Construction of Plasmids for Expression of B1(dsFv)-PE33

In order to construct an active recombinant immunotoxin that was smaller than the current generation of recombinant immunotoxins and that did not need intracellular proteolytic cleavage for activation, the antibody fragment B1(dsFv) was inserted between domains II and III of a Pseudomonas exotoxin. This was accomplished by substituting B1(dsFv) for domain Ib of PE37, a truncated form of PE that contains only the portion of the toxin that undergoes translocation to the cytosol. In particular, B1($V_H$)R44C was inserted after amino acid 364 of PE and the insert was preceded by a small flexible peptide linker GGGGS (SEQ ID NO:12). Following the $V_H$ domain was another peptide, KASGGPE (SEQ ID NO:11) (C3 connector) (Brinkmann et al., *Proc. Natl. Acad. Sci. USA,* 89: 3075–3079 (1992)), connecting the carboxyl terminus of $V_H$ to amino acid 395 of the Pseudomonas exotoxin.

As shown in FIG. 1, the $V_H$ domain replaced amino acids 365 to 394 of PE37 and the $V_L$ domain was connected to the $V_H$ domain by a disulfide bond engineered into the framework region, with cysteines introduced at position 44 of the $V_H$ and position 105 of $V_L$ (Brinkmann et al., *Proc. Natl. Acad. Sci. USA,* 90: 7538–7542 (1993)). The resulting recombinant immunotoxin, termed B1(dsFv)-PE33, is 5 kDa smaller than B1(dsFv)PE38 or B1(Fv)-PE38 (FIG. 1). In the toxin portion, cysteine 287 was changed to a serine to reduce the chance of incorrect disulfide bond formation (Theuer et al., *J. Urol.* 149: 1626–1632 (1993)).

The construction of plasmids pDF1, which encodes PE37, which starts at methionine followed by PE amino acids 281–613 (a truncated form of PE that does not require proteolytic activation), and pB1$V_H$R44C-PE38 which encodes the single-domain B1($V_H$)R44C-PE38 immunotoxin have been described (Theuer et al.,*J. Biol Chem.* 267: 16872–16877 (1992), Benhar et al. *Clin. Cancer Res.* 1: 1023–1029 (1995)). Sticky feet-directed mutagenesis (Clackson et al., *Nucl. Acids Res.* 17: 10163–10170 (1989)) using uracil-containing pDF1 as a template was used to construct the expression plasmid encoding for B1($V_H$) R44C-PE33, the component of the intramolecularly-inserted dsFv-immunotoxin. The B1($V_H$)R44C DNA was PCR amplified using the plasmid pB1$V_H$R44C-PE38 as a template and oligo primers CT119 with 5'-phosphorylated CT120. The forward PCR primer CT119: 5'-GGCAACGACGAGGC CGGCGCGGCCAACGGCG-GTGGC GGATCCGAGGTGCAGCTGGTGGAATCTGGA3' (SEQ. ID NO:41) had sequences that are identical to the DNA encoding for PE residues 356–364 and a peptide linker GGGGS inserted at the 5' end of $V_H$ and a BamHI site was created (underlined). The reverse PCR oligonucleotide primer CT120: 5'-GTCGCCGA GGAACTCCGCGC-CAGTGGGCTCGGGACCTCCGGAAGCT TITGC-3' (SEQ ID NO:2) and sequences that are complementary to the DNA encoding for PE residues 395–403 and a Fv-toxin junction (connector) inserted at the 3' end of $V_H$ and a HindIII site was created (underlined).

The PCR product was purified and annealed to a uracil-containing single-stranded DNA prepared by the rescue of PDF1 phagemid with an M13K07 helper phage (Bio-Rad). The DNA was extended and ligated according to the MUTA-GENE mutagenesis kit (Bio-Rad). Because the annealing efficiency of the PCR fragment to the single-stranded template and the mutagenesis efficiency were low (~10%), the DNA pool used in the mutagenesis reaction was digested with a restriction endonuclease which cuts an unique site in domain Ib region but not in B1($V_H$). This extra digestion step increased the mutagenesis efficiency to more than 50%.

Correct clones were identified by DNA restriction analysis and verified by DNA sequencing. The resulting immunotoxin clone was named pB1($V_H$)R44C-PE33 or pCTK104, which encodes a single-domain B1($V_H$) immunotoxin in which the $V_H$ domain is replaced for the domain Ib region (amino acids 365 to 394) of PE37. The plasmid pB1V$_L$A105CSTOP encodes B1(V$_L$)A105C, which is a component of dsFv-immunotoxin as described previously (Benhar, et al. *Clin. Cancer Res.,* 1: 1023–1029 (1995)).

B) Production of Recombinant Immunotoxin

The components of the disulfide-stabilized immunotoxins B1(V$_H$)R44C-PE38, B1(V$_H$)R44C-PE33, B1(V$_L$)A105C, or single-chain immunotoxin B1(Fv)-PE38 were expressed in separate *E. coli* BL21(λDE3) (Studier, et al., *J. Mol Biol.,* 189: 113–130 (1986)) cultures harboring the corresponding expression plasmid. All recombinant proteins accumulated in inclusion bodies. Disulfide stabilized immunotoxins were obtained by mixing equimolar amounts of solubilized and reduced inclusion bodies essentially as described (Reiter et al., *Cancer Res.,* 54: 2714–2718 (1994)), except that the final oxidation step was omitted and refolding was carried out at pH 9.5. Properly folded disulfide-stabilized and single-chain immunotoxins were purified by sequential ion exchange (Q-Sepharose and Mono Q) followed by size exclusion chromatography on a TSK G3000SW (Toso Haas) column.

The proteins obtained were over 95 % homogeneous and had the expected molecular mass of 59 kDa on SDS-PAGE. In the presence of the reducing agent β-mercaptoethanol, the dsFv-immunotoxin, B1(dsFv)-PE33, was reduced into two species; one is B1(VL105C) and the other is B1(V)-PE33. The apparent molecular weights of these components are 13 kDa and 46 kDa, respectively. The single-domain B1($V_H$)-PE33 immunotoxin was also made and purified. The yield of either B1(dsFv)-PE33 or B1($V_H$)-PE33 was 8–10% of the protein present in inclusion bodies.

C) Cytotoxic Activity of B1(dsFv)-PE33 Toward B1-antigen Expressing Cell Lines

The cytotoxicity of B1(dsFv)-PE33 was determined by measuring the reduction in the incorporation of ($^3$H)-leucine by various human cancer cell lines after treatment with immunotoxin (Kuan et al. *J. Biol. Chem.,* 269: 7 B1(dsFv)-PE38 and B1(V,)-PE33 (no light chain) were included for comparison. Table 1 shows that all three proteins are cytotoxic to cells expressing B1antigen (e.g. A431, MCF7, CRL1739, and LNCaP) but not to cells that do not bind MAb B1 (e.g. L929 and HUT102).

TABLE 1

Cytotoxicity of B1 immunotoxins toward various cell lines.

| | | Antigen[3] | Cytotoxicity[1] $IC_{50}$ ng/ml | | |
|---|---|---|---|---|---|
| Cell Line[2] | Cancer type | Expression | B1(dsFv)PE38 | B1(dsFv)P33 | B1($V_H$)PE33 |
| A431 | epidermoid | +++ | 0.5 | 0.25 | 2.0 |
| MCF7 | breast carcinoma | +++ | 0.9 | 0.35 | 4.0 |
| CRL1739 | gastric | +++ | 0.4 | 0.31 | N.D.[4] |
| LNCaP | prostate | + | 7.0 | 1.3 | N.D.[4] |
| HUT102 | T-cell leukemia | – | >1000 | >1000 | >1000 |
| L929 | mouse fibroblast | – | >1000 | >1000 | >1000 |

[1]Cytotoxcity data are given as $IC_{50}$ values, where $IC_{50}$ is the concentration of immunotoxin that causes a 50% inhibition of protein synthesis after a 20 hour incubation with the immunotoxin.
[2]All of the cell lines except L929 are of human origin.
[3]The level of antigen is marked +++, + and – for strong, medium and no detectable expression respectively.
[4]Not determined.

In this assay, B1(dsFv)-PE33 had an $IC_{50}$ of 0.25 ng/ml on A431 cells and 0.35 ng/ml on MCF7 cells. B1(dsFv)-PE33 was more active to all antigen-positive cell lines in this study than B1(dsFv)-PE38 which requires processing proteolysis. To analyze whether the cytotoxicity of B1(dsFv)-PE33 was specific, competition experiments were carried out with an excess of MAb B1.

The resulting data showed that the intoxication of A431 carcinoma cells by B1(dsFv)-PE33 was due to the specific binding to the B1 antigen, since its cytotoxicity was blocked by excess MAb B1. B1($V_H$)-PE33 that was not associated with light chain was also tested and it proved to be about 10-fold less cytotoxic ($IC_{50}$ 2 ng/ml on A431 cells) than B1(dsFv)-PE33 (Table 1) indicating the heavy chain has a large role in antigen binding. However, a related single-domain immunotoxin (B3($V_H$)-PE38) which requires proteolytic processing for activation was much less active with an $IC_{50}$ of 40 ng/ml on A431 cells (Brinkmaann et al., *J. Immunol.* 150, 2774–2782 (1993)).

D) Antigen Binding of B1(dsFv)-PE33

To determine whether the improved cytotoxicity of B1(dsFv)-PE33 was due to improved binding or some other factor, the antigen binding affinity of B1(dsFv)-PE33 on antigen-positive cells (e.g., A431 cells) determined by competition assays, in which increasing concentrations of each immunotoxin competed for the binding of ($^{125}$I)-B1-IgG to A431 cells at 4° C. B1IgG, B1(dsFv)-PE38, B1(dsFv)-PE33 and B1($V_H$)-PE33 competed for the binding of ($_{124}$I)-B1-IgG to A431 cells by 50% at 40 nM, 2 mM, 3.5 mM, and 25 mM, respectively. Thus, the binding affinity of B1(dsFv)-PE33 was slightly less than B1(dsFv)-PE38 suggesting that the improved cytotoxicity was not due to improved binding, but rather that elimination of the requirement for proteolytic activation was responsible for the improved cytotoxicity. The single-domain immunotoxin B1($V_H$)- P33 exhibited a 10-fold lower binding affinity relative to the dsFv-immunotoxins consistent with its diminished cytotoxicity (Table 1).

E) Stability of B1(dsFv)-PE33

Thermal stability of the immunotoxins was determined by incubating them at 100 μg/ml in PBS at 37° C. for 2 or 8 hours, followed by analytical chromatography on a TSK G3000SW (Toso Haas) column to separate the monomers from larger aggregates (Reiter et al. *Protein Eng.,* 7: 697–704 (1994)). Relative binding affinities of the immunotoxins were determined by adding $^{125}$I-labeled B1-IgG to 10 A431 cells as a tracer with various concentrations of the competitor. The binding assays were performed at 4° C. for 2 h in RPMI containing 1% bovine serum albumin and 50 mM MES (Sigma) as described (Batra et al., *Proc. Natl. Acad. Sci. USA* 89: 5867–5871 (1992)).

Both B1(dsFv)-PE33 and B1(dsFv)-PE38 were monomers before incubation in PBS at 37° C. and remained monomeric for 2 or 8 hrs. In contrast, the single-chain immunotoxin B1(Fv)PE38 formed >60% aggregates after an 8 hr incubation at 37° C. (Table 2, see also et al., *Clin. Cancer Res.*, 1: 1023–1029 (1995)). Following the 8 hr incubation at 37° C., B1(dsFv)-PE33 and B1(dsFv)-PE38 retained almost all its initial cytotoxic activity as before incubation, while B1(Fv)-PE38 lost 75% of its cytotoxic activity. Thus, both B1(dsFv)-PE38 and B1(dsFv)-PE33 are extremely stable at 37° C. presumably because they do not tend to denature and aggregate as do the scFV immunotoxins.

F) Toxicity and Antitumor Activity in Nude Mice

The single dose mouse $LD_{50}$ was determined using female BALB-c mice (6–8 weeks old~20 gm) which were given a single i.v. injection of different doses of B1(dsFv) PE38 or B1(dsFv)PE33 diluted in 200 μl of PBS-HSA. Mice were followed for two weeks after injection. Athymic (Nu-Nu) mice, female 6–8 weeks old~20 gm, were injected subcutaneously on day 0 with $3\times10^6$ A431 cells suspended in RPMI medium without FBS. By day 5, tumors were about 50 to 70 mm³ in size. Mice were treated on days 5, 7, and 9 by i.v. injections of different doses of immunotoxins diluted in PBS-HSA. Tumors were measured with a caliper and the tumor volumes were calculated using the formula: volume=(length)×(width)²×(0.4).

The $LD_{50}$ of both immunotoxins was found to be 0.5 mg/kg. The toxicity is the same as the $LD_{50}$ value determined for the B1(Fv)-PE38 as well as other anti-Le$^y$ Fv-immunotoxins (Reiter et al. *Cancer Res.*, 54: 2714–27 (1994)). The results show that even though the immunotoxin is more active to target cells because it does not require proteolytic activation, it is not more toxic to mice. This toxicity in mice is presumed to be due to non-specific uptake by the liver (Keritman et al., *Blood*, 83: 426–434 (1994).

G) Improved Antitumor Activity of B1(dsFv)-PE33

To determine whether the improved cytotoxicity in vitro is accompanied by an increase in antitumor activity, B1(dsFv)-PE33 and B1(dsFv)-PE38 were compared by assessing their ability to cause regressions of established human carcinoma xenografts in nude mice. Nude mice received $3\times10^6$ A431 cells subcutaneously on day 0. Five days later, when tumors averaged 50–70 mm³ in volume, the mice were treated with three i.v. injections on days 5, 7, and 9 of various doses of immunotoxin. Control mice were treated with PBS-HSA only.

Figure 4:
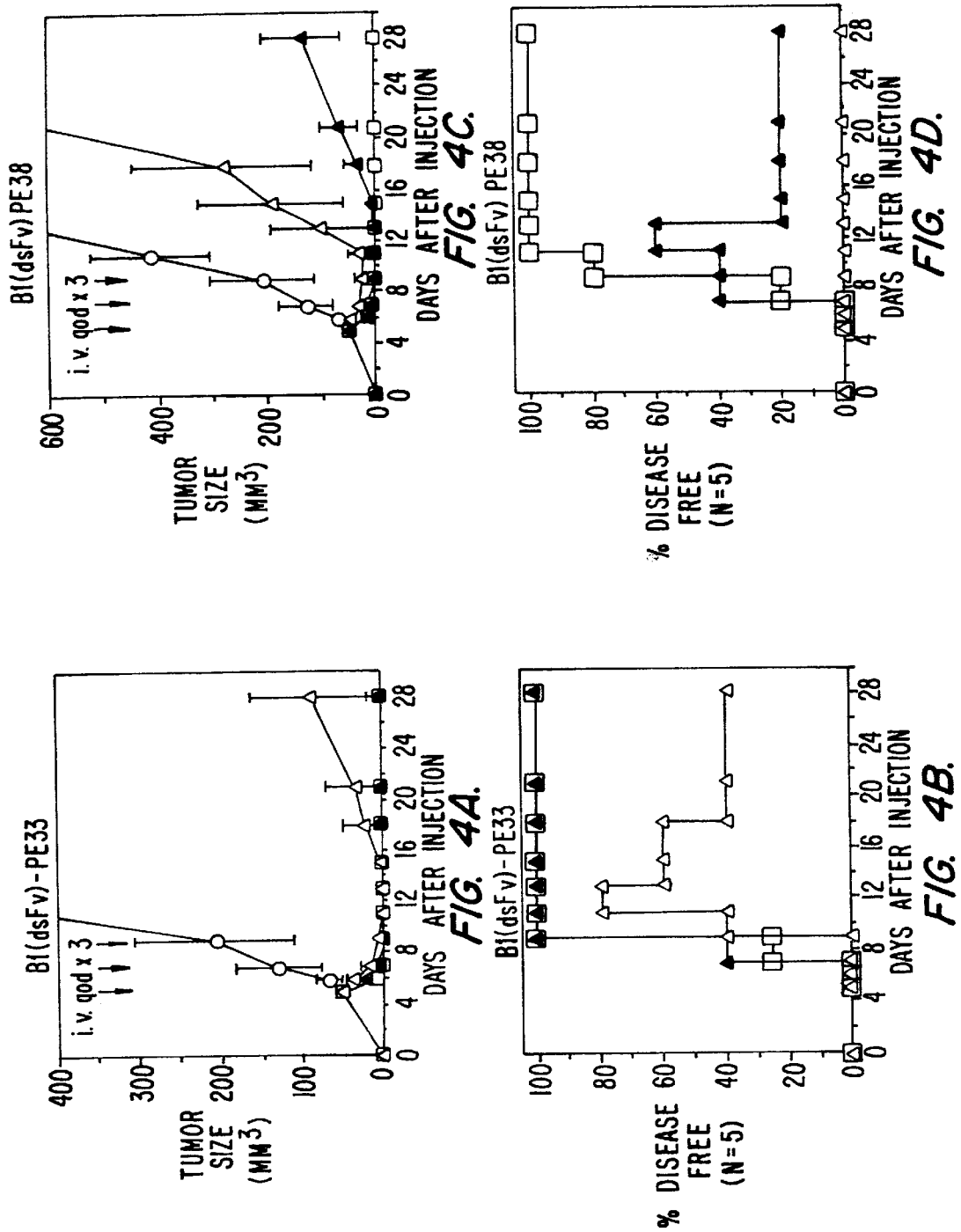
FIG. 4 shows the anti-tumor effect and durability of complete remissions caused by B1 (dsfv)PE33 and B1(dsFv)PE38 in a nude mouse model. Group of five mice were injected s.c. with 3×10$^6$ on day 0 and were treated by i.v. injections of (A) B1(dsFv)PE33 or (B) B1(dsFv)PE38 on days 5, 7, and 9 (indicated by vertical arrows) when the tumors were established. Control mice were treated with PBS-HSA. Error bars represent the standard error of the data. (○) Control; (□) 400 pmole/kg; (▲) 200 pmole/kg; (Δ) 100 pmole/kg.

As shown in FIG. 4, both immunotoxins demonstrated significant dose-dependent anti-tumor activity. B1(dsFv)-PE38 caused only partial regression of A431 tumors at the 6.5 μg/kg (100 pmole/kg) dose level, whereas B1(dsFv)-PE33 at the same 100 pmole/kg (6 μg/kg) dose caused complete disappearance of the tumors (FIG. 4). Furthermore, the tumors treated with 200 pmole/kg (13 μg/kg) B1(dsFv)-PE38 regressed completely after the third injection but regrew within a few days whereas 200 pmole/kg B1(dsFv)-PE33 caused complete regressions that lasted over one month in 5 out of 5 animals. These results indicate that B1(dsFv)-PE33 has significantly better antitumor activity than B1(dsFv)-PE38. Hence, the improved cytotoxicity in vitro correlates with the improved antitumor activity in animals.

Since both B1(dsFv)-PE33 and B1(dsFv)-PE38 have the same toxicity in mice, the PE33 version has a larger therapeutic window. The effective dose causing complete remissions in nude mice is 2.5% of the mouse $LD_{50}$. This makes B1(dsFv)-PE33 a good candidate for clinical development as an anti-cancer agent. The improved antitumor activity of B1(dsFv)-PE33 over B1(dsFv)-PE38 is a consequence of better cytotoxicity in vitro, due to lack of a requirement for proteolytic activation and smaller size for better tumor penetration. Since the efficiency of proteolytic activation can vary in different types of cells, this new type of recombinant immunotoxin will prove more useful than the previous generation of molecules which require proteolytic activation.

In the foregoing experiments, the B1 dsFv fragment was inserted between the translocation domain and ADP-ribosylation domain of PE, replacing domain Ib. In fact, it is also possible to delete a portion of domain II (amino acids 343–364) without loss of activity. In addition, analyses of the proposed structure of B1(dsFv)PE33 using computer graphics shows that the domain Ib region is a good location for insertion of dsFv fragment because the CDRs should still be free to interact with antigen. The results in the foregoing experiments indicate that the presence of B1(dsFv) in this region -only minimally affected antigen binding to A431 cells.

Example 2

Preparation and Testing of PE35/e23(dsFv)KDEL

In order to construct an active recombinant immunotoxin that was smaller than the current generation of recombinant immunotoxins and that did not need intracellular proteolytic cleavage for activation the e23(dsFv) antibody fragment was inserted near the carboxyl terminus of PE35KDEL, a truncated form of PE that contains only the portion of the toxin that undergoes translocation to the cytosol (FIG. 2).

A) Construction of Plasmids

Figure 3:
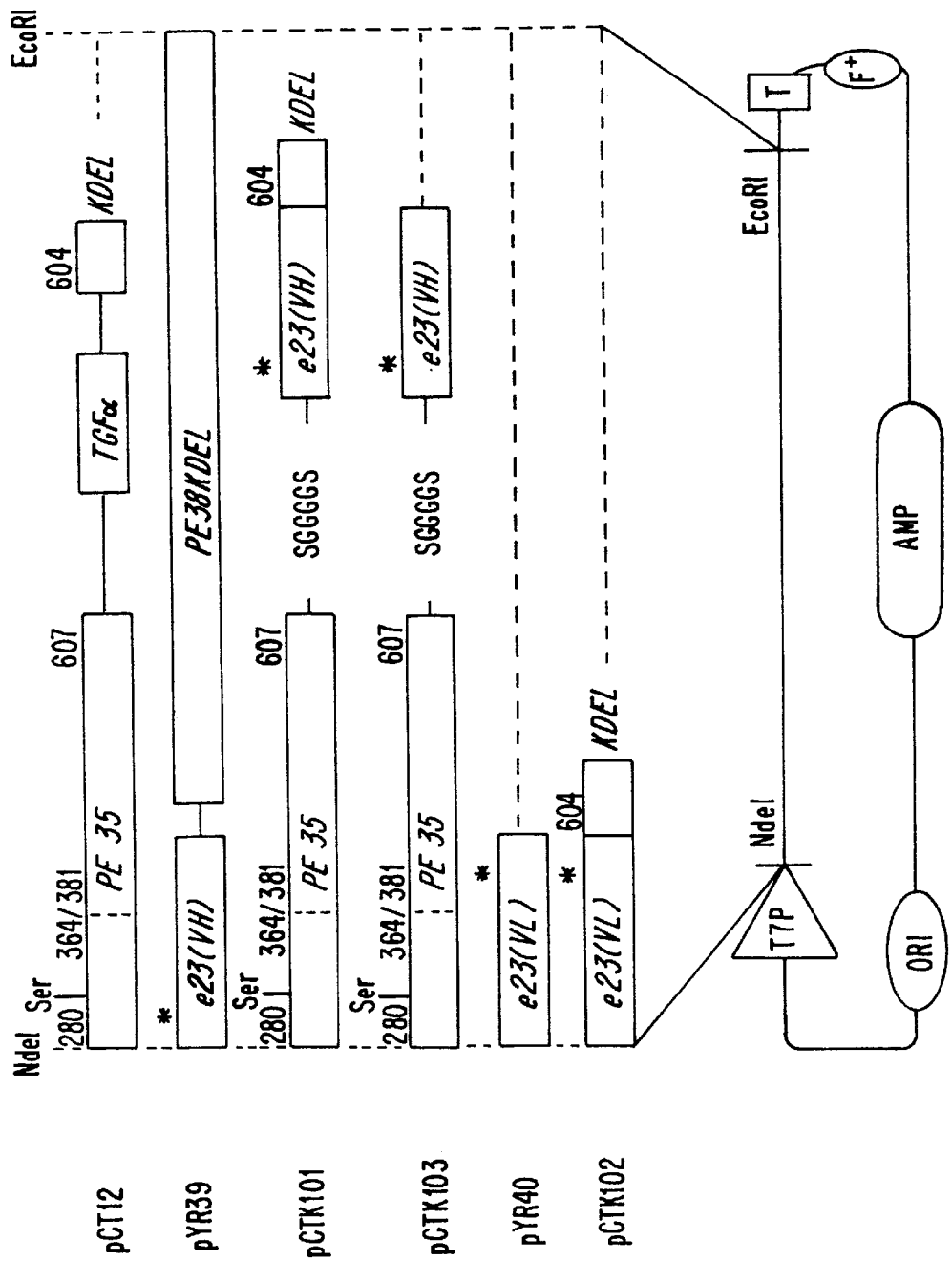
FIG. 3 illustrates the plasmids used for expression of e23 dsfv immunotoxins. Positions of cysteine replacement (shown as asterisk star) in framework region of e23(Fv) are Asn$^{44}$→Cys in $V_H$ and Gly$^{99}$→Cys in $V_L$. Plasmid pCT12 encodes a protein termed PE35/TGFαKDEL, starting with a Met at position 280 of PE and containing amino acids 281 to 364 and 381 to 607 with a gene encoding TGFα inserted between amino acid 607 and 604 of PE, and the carboxyl-terminal amino acids KDEL (SEQ ID NO:9) are substituted for the native REDLK sequence (SEQ ID NO:8). Plasmid pCTK101 and pCTK103, encoding PE35/e23($V_H$Cys$_{44}$)KDEL and PE35/e23($V_H$Cys$_{44}$), respectively, are the expression plasmid for the toxin-$V_H$ components of the dsfv immunotoxin PE/e23(dsfv)KDEL (SGGGGS=SEQ ID NO:10). Plasmid pCTK102 encodes e23($V_L$) Cys 99 fused to PE amino acids 604–608 and carboxyl terminal sequences KDEL (SEQ ID NO:9). Plasmids pYR39 and pYR40 encode e23($V_H$Cys$_{44}$)PE38KDEL and e23($V_L$Cys$_{99}$), respectively.

All plasmids listed in FIG. 3 use an isopropyl-l-thio-β-D-galactopyranoside-inducible 17 promoter expression system (Studier & Moffatt *J. Mol Biol.* 189, 113–130 (1986)). Plasmid pCT12 encodes for a protein, termed PE35/TGFαKDBL, starting with a Met at position 280 of PE and amino acids 281 to 364 and 381 to 607 with a gene encoding TGFα inserted between amino acids 607 and 604 of PE, and the amino acids KDEL are substituted for the carboxyl-terminal REDLK sequence of PE (Theuer et al., *J. Urol.*, 149: 1626–1632 (1993)). Plasmid pYR39, encoding e23 ($V_H$Cys$_{44}$)-PE38KDEL, is the expression plasmid for the $V_H$-Toxin components of the dsFv-immunotoxin e23(dsFv)-PE38KDEL (Reiter et al., *J. Biol. Chem.*, 269: 18327–18331 (1994)). Plasmids pCTK101 and pCTK103 encoding PE35/e23($V_H$Cys$_{44}$)KDEL and PE35/e23($V_H$ Cys$_{44}$) are the expression plasmids for the Toxin-$V_H$ components of the dsFv-immunotoxin PE/e23(dsFv)KDEL. They were constructed by cloning the StuI-EcoRI digested PCR fragments into StuI-EcoRI restriction sites in pCT12. The PCR reactions were carried out using 10 ng of pYR39 as template and 100 pmoles of primers 5'-AAACCGAGGCCTTCCGGA GGTGGTGGATCCGAAGTGCAGCTGCAGGAGTCA GGA-3' (SEQ ID NO:3) and 5'-TTAGCAGCCGAATTC TrAGAGCTCGTCTTTCGGCGGTTGCCGGAGGAGA CGGTGACCGTGGTCCCTG-3' (Seq ID NO:-4) for PE35/e23($V_H$Cys$_{44}$)KDEL or 5'-AAACCGAGGCCTTC CGGAGGTGGTGGATCCGAAGTGCAGCTGCAGGA GTCAGGA-3' (SEQ. ID NO: 5) and 5'-GATCGCTCGG AATTCTTAGGAGACGGTGACCGTGGTCCCTGC-3' (SEQ ID NO:6) for PE35/e23($V_H$ Cys$_{44}$). The protein encoded by pCTK101 is a single-domain immunotoxin in which e23($V_H$ Cys$_{44}$) was introduced between residue 607 of PE followed by a peptide linker SGGGGS and residue 604 to 608 and KDEL. The protein encoded by pCTK103 was the same as pCTK101 encoded protein except without amino acid 604 to 608 and KDEL.

Plasmid pYR40 encodes e23($V_L$ $Cys_{99}$), the $V_L$ component of the dsFv-immunotoxin (Reiter et al., *J. Biol. Chem.* 269, 18327–18331 (1994)), while pCTK102 encodes e23 ($V_L$ $Cys_{99}$) fused to PE amino acids 604–608 and carboxyl terminal sequences KDEL. This plasmid was constructed by subcloning a NdeI-EcoRI digested PCR product, which used pYR40 as template and T7 promoter primer as well as 5'-TTAGCAGCCGAATTCTTAGAGCTCGTCTTTTCGG CGGTTTGCCGGAGGAGACGGTGACCGTGGTCC CTG-3' (SEQ ID NO:7) as primers, into NdeI-EcoRI restriction sites found in pYR40. Positions of cysteine replacement in framework region of e23(Fv) are $Asn^{44}$ ->Cys in $V_H$ and $Gly^{99}$ ->Cys in $V_L$ were described previously (Reiter et al., *J. Biol. Chem.* 269: 18327–18331 (1994)). All plasmids were confirmed by DNA sequencing.

The $V_H$ rather than the $V_L$ was inserted near the carboxyl terminus of PE35KDEL, since PE35/e23($V_H$)KDEL (unattached to $V_L$) is less soluble and more likely to precipitate than PE35/e23($V_l$)KDEL not attached to $V_H$ (Brinlrann et al., *J. Immunol.*, 150: 2774–2782 (1993); Reiter et al., *Biochem.*, 33: 5451–5459 (1994)). The disulfide bond forms between cysteines introduced at position 44 of the $V_H$ and position 99 of $V_L$ (Reiter et al., *J. Biol. Chem.*, 269: 18327–18331 (1994)). In the toxin portion, cysteine 287 was changed to a serine to reduce the chance of incorrect disulfide bond formation (Theuer et al., *J. Urol.*, 149: 1626–1632 (1993); FIG. 2). The location chosen for e23 ($V_H CYS_{44}$) insertion was after amino acid 607 of PE and it was preceded by a small peptide linker SGGGGS (SEQ ID NO:10). Following the $V_H$ domain are amino acids 604–608 and KDEL (SEQ ID NO:9)(FIG. 1). A diagram of this molecule, PE35/e23(dsFv)KDEL (I) is shown in FIGS. 2 and 3.

B) Production of Recombinant Proteins

The components of the disulfide-stabilized immunotoxins PE35/e23($V_H$ $Cys_{44}$)KDEL, PE35/e23(H $Cys_{44}$), e23($V_H$ $Cys_{44}$)-PE38KDEL, e23($V_L$ $Cys_{99}$), and e23($V_L$ $Cys_{99}$) KDEL or single-chain immunotoxins were produced in separate *E. coli* BL21(1DE3) (Studier & Moffatt, *J. Mol. Biol.*, 189: 113–130 (1986)) cultures harboring the corresponding expression plasmid (See FIG. 3). All recombinant proteins accumulated in inclusion bodies. Properly folded disulfide stabilized immunotoxins were obtained by mixing equimolar amounts of solubilized and reduced inclusion bodies essentially as described (Reiter et al., *Cancer Res.*, 54: 2714–2718 (1994)), except that the final oxidation step was omitted and refolding was carried out at pH 9.5.

As shown in FIG. 3, PE35/e23(dsFv)KDEL (I) was produced by mixing PE35-e23($V_H$ $Cys_{44}$)KDEL and e23($V_L$ $Cys_{99}$); PE35/e23(dsFv)KDEL (II) was produced by mixing PE35-e23($V_H$ $Cys_{44}$) and e23($V_L$ $Cys_{99}$)KDEL; PE35/e23 (dsFv)KDEL (III) was produced by mixing PE35-e23($V_H$ $Cys_{44}$)KDEL and e23($V_L$ $Cys_{99}$)KDEL; PE35/e23(dsFv) (I) was produced by mixing PE35-e23($V_H$ $Cys_{44}$) and e23($V_L$ Cys99). The immunotoxins were purified by refolding of inclusion bodies in a redox-shuffling buffer. Properly folded disulfide-stabilized and single-chain immunotoxins were purified by sequential ion exchange (Q-sepharose and Mono Q) followed by size exclusion chromatography on a TSK G3000SW (Toso Haas) column.

The proteins obtained were over 95 % homogeneous and had the expected molecular mass on SDS-PAGE (60 kDa). In the presence of the reducing agent b-mercaptoethanol, the dsFv-immunotoxin, PE35/e23(dsFv)KDEL (I) was reduced into two species; one was e23($V_L Cys_{99}$) and the other was a single-domain toxin PE35/e23($V_H$ $Cys_{44}$)KDEL. The apparent molecular weights of these components was, as expected, 13 kDa and 47 kDa, respectively.

C) Specific Cytotoxic Activity of PE35/e23(dsFv)KDEL Toward e23-antigen Expressing Cell Lines The cytotoxicity of PE35/e23(dsFv)KDEL was determined by measuring the reduction in the incorporation of [$^3$H]-leucine by various human cancer cell lines after treatment with serial dilutions of the immunotoxin in PBS containing 0.2% HSA as described previously (Kuan et al., *J. Biol Chem.*, 269: 7610–7616 (1994)). e23(scFv)-PE38KDEL and e23(dsFv)-PE38KDEL were included for comparison. Table 2 shows that a comparison of the activity of the immunotoxin PE35-e23(dsFv)KDEL (1) and the other two reference molecules, e23(scFv)-PE38KDEL and e23 (dsFv)-PE38KDEL, indicates that all three proteins are cytotoxic to cells expressing

TABLE 2

Cytotoxicity of e23 immunotoxins towards various cell lines.

| | | | Cytotoxicity[1] $IC_{50}$ ng/ml | | |
|---|---|---|---|---|---|
| Cell Line | Cancer type | Antigen[2] Expression | e23(scFv) PE38KDEL | e23(dsFv) PE38KDEL | PE35/e23 (dsFv)KDEL (I) |
| N-87 | gastric | +++ | 0.5 | 0.1 | 0.8 |
| A431 | epidermoid | + | 2.9 | 1.0 | 3.0 |
| Hut102W | leukemia | – | >1000 | >1000 | >1000 |

[1]Cytotoxcity data are given as $IC_{50}$ values, where $IC_{50}$ is the concentration of immunotoxin that causes a 50% inhibition of protein synthesis after a 20 hour incubation with the immunotoxin.
[2]The level of antigen is marked +++, + and – for strong, medium and no detectable expression respectively.

erbB2 (e.g. N87 and A431) but not to cells (e.g. HUT-102) that do not bind MAb e23 (Table 2). In this assay, PE35/e23(dsFv)KDEL() had an $IC_{50}$ of 0.8 ng/ml on N87 cells. Although its activity is less than the two other molecules ($IC5_0$ of 0.5 ng/ml for e23(scFv)-PE38KDEL and 0.1 ng/ml for e23(dsFv)-PE38KDEL), it is still extremely active.

D) Improved Stability of Immunotoxin PE35/e23(dsFV) KDEL (I)

Thermal stability of the immunotoxins was determined by incubating them at 100 μg/ml in PBS at 37° C. for 2 or 8 hours, followed by analytical chromatography on a TSK G3000SW (Toso Haas) column to separate the monomers from dimers and larger aggregates. PE35/e23(dsFv)KDEL (1) was a monomer before incubation in PBS at 37° C. and remained monomeric for 2 or 8 hrs. In contrast, the single-chain immunotoxin e23(Fv)PE38KDEL formed 30% aggregates and 25% dimers after an 8 h incubation at 37° C. Following the 8 h 37° C. treatment, PE35/e23(dsFv)KDEL (I) retained almost the same cytotoxic activity as before treatment, while e23(Fv)PE38KDEL had an $IC_{50}$ of 3.1 ng/ml on N-87 cells, which is only 16% of its cytotoxic activity before treatment. This result indicates that the purified PE35/e23(dsFv)KDEL like e23(dsFv)-PE38KDEL (Reiter et al., *Protein Eng.*, 7: 697–704 (1994)) is very stable and has a low propensity to aggregate.

E) Antigen-binding Analysis of PE35/e23(dsFv)KDEL (I)

To investigate the reason for the decreased cytotoxicity of PE35/e23(dsFv)KDEL (I), its antigen binding affinity on antigen-positive cells (e.g., N87 cells) was analyzed by competition assays in which increasing concentrations of each immunotoxin were present to compete for the binding of [$^{125}$I]-e23-IgG to N87 cells at 4° C. The e23 IgG, e23(dsFv)-PE38KDEL, and PE35/e23(dsFv)KDEL competed for the binding of [$^{125}$I]-e23 IgG to N87 cell by 50% at 4 nM, 140 nM and 500 nM, respectively. Thus, the binding affinity of PE35/e23(dsFv)KDEL (1) is 4-fold less than e23(dsFv)-PE38KDEL on N87 cells. Hence, the lower cytotoxicity of PE35/e23(dsFV)KDEL (1) is associated with a lower bivalent binding affinity. As previous reported the bivalent e23IgG had a higher apparent affinity than e23(dsFv)PE38KDEL which is monovalent (Reiter et al., *J. Biol Chem.*, 269: 18327–18331 (1994)).

F) Importance of the Position of KDEL (SEQ ID NO:9) for Cytotoxicity

In PE35/e23(dsFv)KDEL (SEQ ID NO:9) (I), the KDEL is on the same polypeptide chain as the toxin moiety. The KDEL sequence is considered to mediate transport of the toxin moiety of the immunotoxin to the ER where it can translocate. To address whether it was important to have the KDEL (SEQ ID NO:9) sequence on the C-terminus of the toxin, or whether it could be attached to the C-terminus of the $V_L$ which is attached to $V_H$PE35 by a disulfide bond molecules were constructed having KDEL (SEQ ID NO:9) on $V_L$ instead of the $V_H$ toxin, with KDEL (SEQ ID NO:9) on both the $V_H$-toxin and the $V_L$ and with KDEL (SEQ ID NO:9) on neither (FIG. 2). These were termed PE35/e23 (dsFv)KDEL II-IV (Table 3 and FIG. 2). Table 2 shows that for the recombinant toxin to inhibit protein synthesis on target cells, it is

TABLE 3

Comparison of four different types of PE35/e23(dsFv)KDEL.

| Construct | Activity[1] $IC_{50}$ (ng/ml) | Relative binding[1,2] (nM) |
|---|---|---|
| PE35/e23(dsFv)KDEL(I) | 0.8 | 500 |
| PE35/e23(dsFv)KDEL(II) | 1000 | 400 |
| PE35/e23(dsFv)KDFL(IV) | 1.2 | 530 |
| PE35/e23(dsFv)(IV) | >1000 | 610 |

[1]Cytotoxicity and binding assays were measured on N-87 cell line.
[2]The concentration of competitor which caused 50% inhibition of the binding of $^{125}$I-e23 IgG. The composition of I–IV are shown in FIG. 2.

important to have the KDEL (SEQ ID NO:9) on the same polypeptide as the toxin moiety. If no KDEL (SEQ ID NO:9) is present, toxicity is lost. If KDEL (SEQ ID NO:9) is on the $V_L$ domain, cytotoxicity is also lost. The presence of KDEL (SEQ ID NO:9) on $V_L$ in addition to $V_H$-toxin does not change cytotoxic activity. Thus the KDEL (SEQ ID NO:9) sequence must be on the same polypeptide chain as the toxin.

G) Relative Binding Affinities

Relative binding affinities of the immunotoxins were determined by adding $^{125}$I-labeled e23IgG to $10^5$ N87 cells as a tracer with various concentrations of the competitor. The binding assays were performed at 4° C. for 2 h in RPNH containing 1% bovine serum albumin and 50 mM MES (Sigma) as described (Batra et al. *Proc. Natl. Acad. Sci. USA*, 89: 58678–5871 (1992)). Table 3 shows that there is very little difference in binding affinities among the four molecules. Thus the differences in cytotoxicities can be attributed to the location of the KDEL (SEQ ID NO:9) sequence on the toxin molecules.

Example 3

Cytotoxicity and Binding of B3-immunotoxins

Monoclonal antibody B3 is a murine antibody referred to above directed against Lewis$^Y$ and related carbohydrate antigens which are abundant on the surface of many carcinomas. See Example 1 for a fuller description of Lewis$^Y$ antigens.

Figure 5:
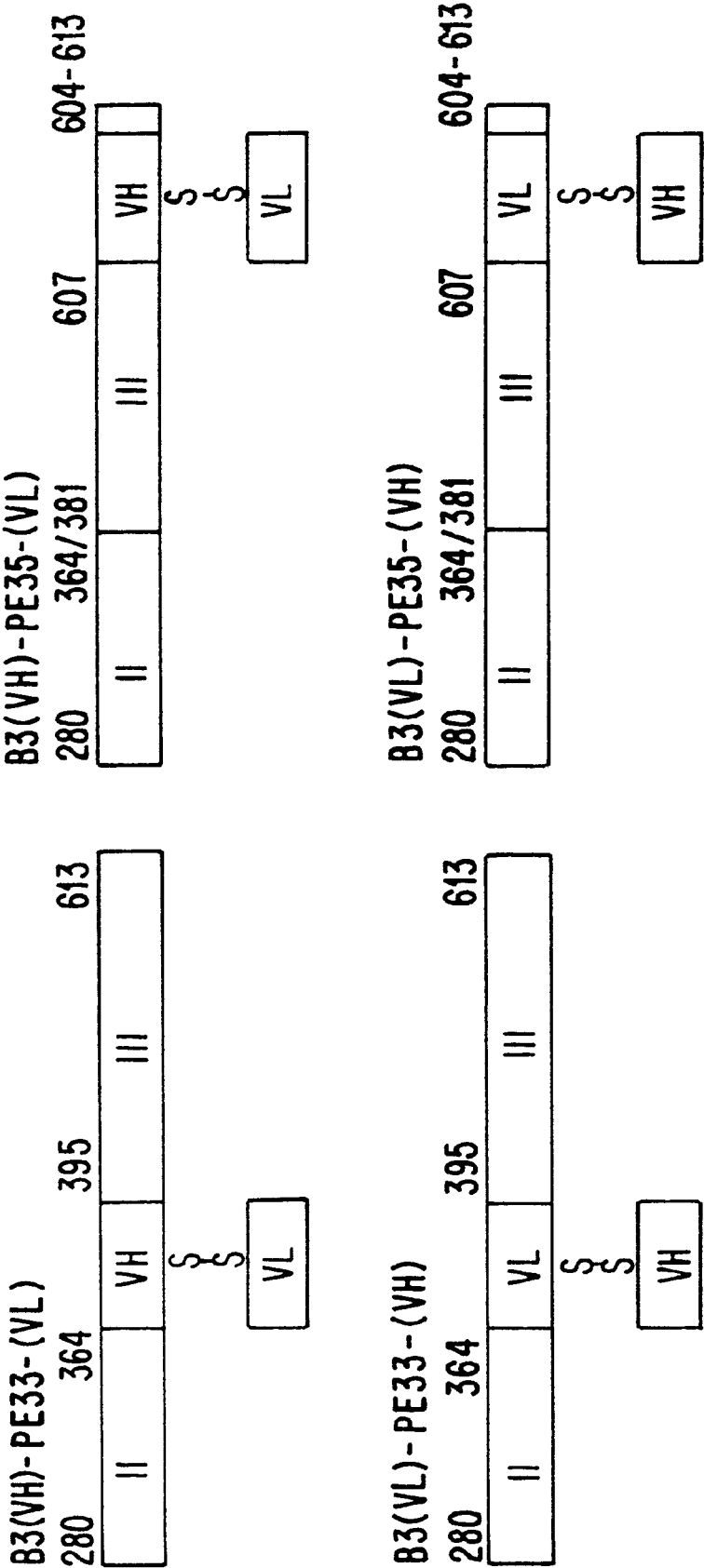
FIG. 5 provides a schematic representation of B3 immunotoxins having a disulfide-stabilized binding agent placed at the carboxy terminus or inserted in place of domain Ib. Positions of amino acids that span PE sequences are numbered. S—S shows the disulfide bond linkage between the Fv fragments. $V_H$: variable heavy chain; $V_L$: variable light chain; II: PE domain II for translocation; III: PE domain III for ADP-ribosylation of EF2.

To evaluate the binding affinities and cytotoxic effect on cancer cells, PE with amino acids 1–279 of the amino terminus deleted were modified by inserting variable regions of either B3 heavy or light chains. The insertions were made as described above in the Ib domain or at the carboxyl terminus of domain III. See FIG. 5 for a schematic of the B3 immunotoxins.

A) Cytotoxic Activity of B3-immunotoxins Toward B3-antigen Expressing Cell Lines The cytotoxicity of B3-immunotoxins was determined by measuring the reduction in the incorporation of ($^3$H)-leucine by A431 cells after treatment with immunotoxin Kuan et al. *J. Biol Chem.*, 269: 7610–7616 (1994)). A comparison of B1 immunotoxins (see Table 1) indicates that the B3-immunotoxins are less cytotoxic than the B1constructs. As Table 4 shows, this decrease in cytotoxicity is likely due in part to decreased binding affinity.

B) Binding Affinities of B3-immunotoxins

To determine relative binding affinities, increasing concentrations of each immunotoxin competed for the binding of ($^{125}$I)-B3-IgG (or B1-IgG for comparison) to A431 cells at 4° C. for 2 hours in RPM' containing 1% bovine serum albumin and 50 mM MES as described (Batra et al. *Proc. Nat'l. Acad. Sci. USA*, 89: 58678 (1992)).

TABLE 4

Cytotoxicity and binding of B3-immunotoxins on A431 cells

| Construct | A431 ($IC_{50}$ ng/nM) | Binding (nM) |
|---|---|---|
| B3(Fv)-PE38 (LMB7) | 1~1.5 | 550 |
| B3(dsFv)PE38 | 1~1.5 | 25,000 |
| B3(VH)-PE35-(VL) | 110 | >30,000 |
| B3(VL-PE35-(VH) | 100 | 6,000 |
| B3(VH)-PE33-(VL) | 5 | 30,000 |
| B3(VL)-PE33-(VH) | 50 | 5,000 |
| B3-IgG | | 150 |

TABLE 5

Cytotoxicity and binding of B3∂B1-immunotoxins on A431 cells

| Protein | A431 (IC$_{50}$ ng/nM) | Binding (nM) |
|---|---|---|
| B3(VH)-PE38-(VL) | 1~1.5 | 25,000 |
| B3VH)-PE35-(VL) | 110 | >30,000 |
| B3(VL)-PE3S-(VH) | 100 | 6,000 |
| B3(VH)-PE33-(VL) | 5 | 30,000 |
| B3(VL)-PE33-(VH) | 50 | 5,000 |
| B3(Fv)-PE38 | 1~1.5 | 550 |
| B3-IgG | | 150 |
| Construct | | |
| B1(VH)-PE38-(VL) | 0.5 | 2,000 |
| B1(VH)-PE33-(VL) | 0.25 | 3,500 |
| B1(VH)-PE33 | 2.0 | 25,000 |
| B1-IgG | | 40 |

Example 4

Cytotoxicity and Binding of e23-immunotoxins on Cancer Cells

Monoclonal antibody e23 is a murine antibody directed against erbB2 antigen. See Example 2 for a fuller description of the erbB2 antigen and the preparation of e23-immunotoxins.

To evaluate the binding affinities and cytotoxic effect on cancer cells, PE with the first 279 amino acids at the amino terminus deleted were modified by insertion of variable regions of either e23 heavy or light chains. The insertions were made in the Ia domain or at the carboxyl terminus of domain III.

A) Cytotoxic Activity of e23-immunotoxins Against Cancer Cell Lines

The cytotoxicity of e23-immunotoxins was determined by measuring the reduction in the incorporation of [$^3$H]-leucine by MCF7 and N-87 cell lines after treatment with serial dilutions of the immunotoxins in PBS containing 0.2% HSA as described previously (Kuan et al. *J. Biol Chem.*, 269: 7610–7616 (1994)). The results are shown in Table 6.

B) Binding Affinities of e23-immunotoxins

To determine relative binding affinities, increasing concentrations of each immunotoxin competed for the binding of ($^{125}$I)-e23-IgG to MCF7 and N-87 cells at 4° C. for 2 hours in RPMI containing 1% bovine serum albumin and 50 mM MES as described (Batra et al. *Proc. Nat'l. Acad. Sci. USA*, 89: 58678 (1992)). The results are shown in Table 6.

TABLE 6

Cytotoxicity and binding of e23-immunotoxins on cancer cells

| Construct | MCF7 (IC50 ng/ml) | Binding (nM) | N-87 (IC$_{50}$ ng/ml) | Binding (nM) |
|---|---|---|---|---|
| e23(VH)PE38-VL | 3.5 | 110 | 0.35 | 120 |
| e23VL)PE35-(VH) | 15 | 65 | 70 | 110 |
| e23(VL)PE35 | 2.2 | 1,800 | 42 | 2,000 |
| e23(VH)PE33-(VL) | 30 | 320 | 20 | 210 |
| e23(VL)PE33-(VH) | 25 | 115 | 3.6 | 110 |
| e23(VL)PE33 | 70 | 5,000 | 200 | >2,000 |
| e23-IgG | | | | 4 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A nucleic acid encoding an immunotoxin that does not require proteolytic activation for cytotoxic activity, said immunotoxin comprising a Pseudomonas exotoxin (PE) having an amino terminus and a carboxyl terminus, but lacking amino acids 1 through 279, and in which half or more of domain Ib is replaced with part or all of either a variable light ($V_L$) chain of an Fv antibody fragment having an amino terminus and a carboxyl terminus or a variable heavy ($V_H$) chain of an Fv antibody fragment having an amino terminus and a carboxyl terminus, provided that if only a part of a $V_L$ or of a $V_H$ chain is used, said part specifically binds to a target molecule.

2. A nucleic acid of claim 1, wherein half or more of PE domain Ib is replaced with all or part of a variable light chain region.

3. A nucleic acid of claim 1, wherein half or more of PE domain Ib is replaced with all or part of a variable heavy chain region.

4. A nucleic acid of claim 1, wherein the Fv antibody fragment is of an antibody selected from the group consisting of B1, B3, B5, e23, BR96, anti-Tac, RFB4, and HB21.

5. The nucleic acid of claim 1, wherein said immunotoxin has KDEL (SEQ ID NO:9) as a carboxyl terminal sequence of said PE.

6. The nucleic acid of claim 1, wherein said amino terminus of said $V_H$ region or of said $V_L$ region is attached to the PE through a peptide linker.

7. The nucleic acid of claim 1, wherein said peptide linker is SGGGS (SEQ ID NO:10).

8. The nucleic acid of claim 1, wherein the carboxyl terminus of said $V_H$ region or of said $V_L$ region is attached to the PE through a peptide linker.

9. The nucleic acid of claim 1, wherein said peptide linker is KASGGPE (SEQ ID NO:11).

10. A method of killing a cell bearing a target molecule, said method comprising contacting said cells with an immunotoxin comprising a Pseudomonas exotoxin that does not require proteolytic activation for cytotoxic activity and wherein half or more of domain Ib is replaced by part or all of an Fv antibody fragment which specifically binds to the target molecule, said Fv fragment having a variable heavy chain region ($V_H$) and a variable light chain region ($V_L$) which $V_H$ and $V_L$ regions are bound by at least one disulfide bond, whereby said Pseudomonas exotoxin kills said target cell.

11. The method of claim 10 wherein the Fv antibody fragment is from an antibody selected from the group consisting of B1, B3, B5, e23, BR96, anti-Tac, RFB4, and HB21.

12. The method of 10, wherein said immunotoxin has KDEL (SEQ ID NO:9) as a carboxyl terminal sequence of said PE.

13. The method of claim 10, wherein said immunotoxin is selected from the group consisting of B1(dsFv)PE33, B3(VH)-PE33-(VL) and B3(VL)-PE33-(VH).

14. A method of delivering a Pseudomonas exotoxin (PE) to the cytosol of a cell, said method comprising contacting said cell with a chimeric molecule, said chimeric molecule comprising a PE that does not require proteolytic cleavage for cytotoxic activity and a heavy chain variable region or a light chain variable region of a Fv fragment of an antibody which specifically binds to the cell, wherein part or all of said heavy chain variable region or said light chain variable region replaces half or more of domain Ib of said PE, thereby delivering said PE to the cytosol of the cell.

15. The method of claim 14, wherein said variable region of an Fv fragment is of a light chain.

16. The method of claim 15, wherein said light chain is bound by a disulfide bond to a heavy chain variable region of an Fv fragment of an antibody.

17. The method of claim 14, wherein said variable region of an Fv fragment is of a heavy chain.

18. The method of claim 17, wherein said heavy chain is bound by a disulfide bond to a light chain variable region of an Fv fragment of an antibody.

19. The method of claim 14, wherein the Fv fragment of an antibody is from an antibody selected from the group consisting of B1, B3, B5, c23, BR96, anti-Tac, RFB4, and MB21.

20. The method of claim 14, wherein said chimeric molecule has KDEL (SEQ ID NO:9) as a carboxyl terminal sequence of said PE.

21. The nucleic acid of claim 14, wherein said amino terminus of said $V_H$ region or of said $V_L$ region is attached to the PE through a peptide linker.

22. The nucleic acid of claim 21, wherein said peptide linker is SGGGS (SEQ ID NO:10).

23. The nucleic acid of claim 14, wherein the carboxyl terminus of said $V_H$ region or of said $V_L$ region is attached to the PE through a peptide linker.

24. The nucleic acid of claim 23, wherein said peptide linker is KASGGPE (SEQ ID NO:11).

25. The method of claim 14, wherein said immnunotoxin is selected from the group consisting of B1(dsFv)PE33, B3(VL)-PE33-(VH), and B3($V_H$)-PE33-(VL).

* * * * *